United States Patent
Bowen et al.

(10) Patent No.: US 11,266,151 B2
(45) Date of Patent: *Mar. 8, 2022

(54) INSECT INHIBITORY PROTEINS

(71) Applicant: Monsanto Technology LLC, St. Louis, MO (US)

(72) Inventors: David J. Bowen, Wildwood, MO (US); Catherine A. Chay, Ballwin, MO (US); Danqi Chen, Ballwin, MO (US); Todd A. Ciche, San Diego, CA (US); Arlene R. Howe, Clarkson Valley, MO (US); Jennifer L. Lutke, Ballwin, MO (US); Barbara E. Wiggins, Chesterfield, MO (US); Yuanji Zhang, Chesterfield, MO (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/748,392

(22) Filed: Jan. 21, 2020

(65) Prior Publication Data

US 2020/0229445 A1 Jul. 23, 2020

Related U.S. Application Data

(60) Provisional application No. 62/795,066, filed on Jan. 22, 2019.

(51) Int. Cl.
| | |
|---|---|
| *A01N 63/25* | (2020.01) |
| *C12N 15/70* | (2006.01) |
| *C12Q 1/6895* | (2018.01) |
| *C07K 14/195* | (2006.01) |
| *C12N 15/82* | (2006.01) |

(52) U.S. Cl.
CPC ............ *A01N 63/25* (2020.01); *C07K 14/195* (2013.01); *C12N 15/70* (2013.01); *C12N 15/8286* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 7,510,878 B2 | 3/2009 | Abad et al. | |
| 7,772,465 B2 | 8/2010 | Abad et al. | |
| 7,812,129 B1 | 10/2010 | Abad et al. | |
| 10,155,960 B2 * | 12/2018 | Bowen | A01N 63/10 |
| 2006/0021087 A1 | 1/2006 | Baum et al. | |
| 2008/0300210 A1 | 12/2008 | German et al. | |
| 2009/0313721 A1 | 12/2009 | Abad et al. | |
| 2010/0077507 A1 | 3/2010 | Abad et al. | |
| 2010/0077508 A1 | 3/2010 | Abad et al. | |
| 2010/0192256 A1 | 7/2010 | Abad et al. | |
| 2010/0269221 A1 | 10/2010 | Abad et al. | |
| 2011/0112013 A1 | 5/2011 | Abad et al. | |
| 2011/0154536 A1 | 6/2011 | Abad et al. | |
| 2012/0047606 A1 | 2/2012 | Abad et al. | |
| 2012/0167259 A1 | 6/2012 | Liu et al. | |
| 2013/0097735 A1 | 4/2013 | Bowen et al. | |
| 2017/0058294 A1 | 3/2017 | Bowen et al. | |
| 2018/0002386 A1 * | 1/2018 | Bowen | A01N 63/10 |

OTHER PUBLICATIONS

Guo et al, 2004. "Protein tolerance to random amino acid change". Proc. Natl. Acad. Sci. USA 101: 9205-9210 (Year: 2004).*
Kennel, D.E. "Principles and practices of nucleic acid hybridization". Progr. Nucleic Acid Res. Mol. Biol. 11: 259-301. (Year: 1971).*
Pigott, et al., "Role of Receptors in Bacillus thuringiensis Crystal Toxin Activity," Microbiology and Molecular Biology Reviews, 2007, 71(2), 255-281.
Ochoa-Campuzano, et al., "An ADAM metalloprotease is a Cry3Aa Bacillus thuringiensis toxin receptor," Biochemical and Biophysical Research Communication, 2007, 362(2): 437-442.
Yu, et al., "The "how" and "where" of plant microRNAs," New Phytologist, 2017, 216, 1002-1017.
Invitation to Pay Additional Fees regarding International Application No. PCT/US2020/0144437, dated Apr. 8, 2020.
International Search Report and Written Opinion regarding International App. No. PCT/US20/14437, dated Jan. 21, 2020.
UniProtKB Accession No. A0A3A3GLR0_PANTH, CBM-cenC domain-containing protein, dated Dec. 5, 2018.

* cited by examiner

*Primary Examiner* — Matthew R Keogh
*Assistant Examiner* — David R Byrnes
(74) *Attorney, Agent, or Firm* — Dentons US LLP; Timothy K. Ball

(57) ABSTRACT

Pesticidal proteins exhibiting toxic activity against Lepidopteran pest species are disclosed, and include, but are not limited to, TIC7941, TIC7941PL_1, TIC7941PL_2, and TIC7941PL_3. DNA constructs are provided which contain a recombinant nucleic acid sequence encoding one or more of the disclosed pesticidal proteins. Transgenic plants, plant cells, seed, and plant parts resistant to Lepidopteran infestation are provided which contain recombinant nucleic acid sequences encoding the pesticidal proteins of the present invention. Methods for detecting the presence of the recombinant nucleic acid sequences or the proteins of the present invention in a biological sample, and methods of controlling Lepidopteran species pests using any of the TIC7941, TIC7941PL_1, TIC7941PL_2, and TIC7941PL_3 pesticidal proteins are also provided. Also disclosed are methods and compositions to improve the insecticidal activity of a pesticidal protein against an insect pest species. Further disclosed are method and compositions to reduce expression of a pesticidal protein in the reproductive tissues of a transgenic plant.

23 Claims, No Drawings

Specification includes a Sequence Listing.

INSECT INHIBITORY PROTEINS

REFERENCE TO RELATED APPLICATION

This application claims the benefit of U.S. provisional application No. 62/795,066, filed Jan. 22, 2019, which is herein incorporated by reference in its entirety.

INCORPORATION OF SEQUENCE LISTING

The file named "MONS469US_ST25.txt" containing a computer-readable form of the Sequence Listing was created on Jan. 21, 2020. This file is 84,760 bytes (measured in MS-Windows®), filed contemporaneously by electronic submission (using the United States Patent Office EFS-Web filing system), and incorporated by reference in its entirety.

FIELD OF THE INVENTION

The invention generally relates to the field of insect inhibitory proteins. A novel class of proteins exhibiting insect inhibitory activity against agriculturally-relevant pests of crop plants and seeds are disclosed. In particular, the disclosed class of proteins is insecticidally active against agriculturally-relevant pests of crop plants and seeds, particularly Lepidopteran species of insect pests. Plants, plant parts, and seeds containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera and Coleoptera, are considered a major cause of damage to field crops, thereby decreasing crop yields over infested areas. Lepidopteran pest species which negatively impact agriculture include, but are not limited to, Black armyworm (*Spodoptera exempta*), Black cutworm (*Agrotis ipsilon*), Corn earworm (*Helicoverpa zea*), Cotton leaf worm (*Alabama argillacea*), Diamondback moth (*Plutella xylostella*), European corn borer (*Ostrinia nubilalis*), Fall armyworm (*Spodoptera frugiperda*), Cry1Fa1 resistant Fall armyworm (*Spodoptera frugiperda*), Old World bollworm (OWB, *Helicoverpa armigera*), Southern armyworm (*Spodoptera eridania*), Soybean looper (*Chrysodeixis includens*), Spotted bollworm (*Earias vittella*), Southwestern corn borer (*Diatraea grandiosella*), Tobacco budworm (*Heliothis virescens*), Tobacco cutworm (*Spodoptera litura*, also known as cluster caterpillar), Western bean cutworm (*Striacosta albicosta*), and Velvet bean caterpillar (*Anticarsia gemmatalis*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of additional bacterial species, such as *Brevibacillus laterosporus*, *Lysinibacillus sphaericus* ("Ls" formerly known as *Bacillus sphaericus*), *Paenibacillus popilliae* and *Paenibacillus lentimorbus*.

Crystalline and secreted soluble insecticidal toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal toxin proteins has been globally adapted. For example, in 2016, 23.1 million hectares were planted with transgenic crops expressing Bt toxins and 75.4 million hectares were planted with transgenic crops expressing Bt toxins stacked with herbicide tolerance traits (ISAAA. 2016. *Global Status of Commercialized Biotech/GM Crops: 2016.ISAAA Brief No. 52. ISAAA: Ithaca, N.Y.*). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action reduces the probability of resistance in any single target insect species.

Thus, the inventors disclose herein a novel protein toxin family from *Paenibacillus lentimorbus*, along with similar toxin proteins, variant proteins, and exemplary recombinant proteins that exhibit insecticidal activity against target Lepidopteran species.

SUMMARY OF THE INVENTION

Disclosed herein is a novel group of pesticidal proteins with insect inhibitory activity (toxin proteins), referred to herein as TIC7941 belonging to the TIC7941 protein toxin class, which are shown to exhibit inhibitory activity against one or more pests of crop plants. The TIC7941 protein and proteins in the TIC7941 protein toxin class can be used alone or in combination with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter fragment operably linked to a polynucleotide segment encoding a pesticidal protein or fragment thereof, wherein (a) said pesticidal protein comprises the amino acid sequence of SEQ ID NO:4, SEQ ID NO:2, SEQ ID NO:6; SEQ ID NO:8, SEQ ID NO:10, SEQ ID NO:12, or SEQ ID NO:14; or (b) said pesticidal protein comprises an amino acid sequence having at least 80% or, 85%, or 90%, or 95%, or 98%, or 99%, or about 100% amino acid sequence identity to SEQ ID NO:4, SEQ ID NO:2, SEQ ID NO:6; SEQ ID NO:8, SEQ ID NO:10, SEQ ID NO:12, or SEQ ID NO:14; or (c) said polynucleotide segment hybridizes to a polynucleotide having the nucleotide sequence of SEQ ID NO:3, SEQ ID NO:1, SEQ ID NO:5; SEQ ID NO:7, SEQ ID NO:9, SEQ ID NO:11, or SEQ ID NO:13; or (d) said polynucleotide segment encoding a pesticidal protein or fragment thereof comprises a polynucleotide sequence having at least 65%, or 70%, or 75%, or 80%, or 85%, or 90%, or 95%, or 98%, or 99%, or about 100% sequence identity to the nucleotide sequence of SEQ ID NO:3, SEQ ID NO:1, SEQ ID NO:5; SEQ ID NO:7, SEQ ID NO:9, SEQ ID NO:11, or SEQ ID NO:13; or (e) said recombinant nucleic acid molecule is in operable linkage with a vector, and said vector is selected from the group consisting of a plasmid, phagemid, bacmid, cosmid, and a bacterial or yeast artificial chromosome. The recombinant nucleic acid molecule can comprise a sequence that functions to express the pesticidal protein in a plant; or is expressed in a plant cell to produce a pesticidally effective amount of pesticidal protein.

In another embodiment of this application are host cells comprising a recombinant nucleic acid molecule of the application, wherein the host cell is selected from the group consisting of a bacterial and a plant cell. Contemplated bacterial host cells include *Agrobacterium, Rhizobium, Bacillus, Brevibacillus, Escherichia, Pseudomonas, Klebsiella, Pantoec,* and *Erwinia*. In certain embodiments, said *Bacillus* species is *Bacillus cereus* or *Bacillus thuringiensis,* said *Brevibacillus* is *Brevibacillus laterosperous,* or *Escherichia* is *Escherichia coli*. Contemplated plant host cells include a dicotyledonous plant cell and a monocotyledonous plant cell. Contemplated plant cells further include an alfalfa, banana, barley, bean, broccoli, cabbage, *Brassica,* carrot, cassava, castor, cauliflower, celery, chickpea, Chinese cabbage, citrus, coconut, coffee, corn, clover, cotton (*Gossypium* sp.), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In another embodiment, the pesticidal protein exhibits activity against Lepidopteran insects, including Velvet bean caterpillar, Sugarcane borer, Lesser cornstalk borer, Corn earworm, Tobacco budworm, Soybean looper, Black armyworm, Southern armyworm, Fall armyworm, Beet armyworm, Old World bollworm, Oriental leaf worm, Pink bollworm, Black cutworm, Southwestern Corn Borer, Cotton leaf worm, Diamond back moth, Spotted boll worm, Tobacco cut worm, Western bean cutworm, and European corn borer.

Also contemplated in this application are plants comprising a recombinant nucleic acid molecule comprising a heterologous promoter fragment operably linked to a polynucleotide segment encoding a pesticidal protein or fragment thereof, wherein: (a) said pesticidal protein comprises the amino acid sequence of SEQ ID NO:4, SEQ ID NO:2, SEQ ID NO:12, or SEQ ID NO:14; or (b) said pesticidal protein comprises an amino acid sequence having at least 80% or, 85%, or 90%, or 95%, or 98%, or 99%, or about 100% amino acid sequence identity to SEQ ID NO:4, SEQ ID NO:2, SEQ ID NO:12, or SEQ ID NO:14; or (c) said polynucleotide segment hybridizes under stringent hybridization conditions to the compliment of the nucleotide sequence of SEQ ID NO:3, SEQ ID NO:11, or SEQ ID NO:13; or (d) said plant exhibits a detectable amount of said pesticidal protein. In certain embodiments, the pesticidal protein comprises SEQ ID NO:4, SEQ ID NO:2, SEQ ID NO:12, or SEQ ID NO:14. In one embodiment, the plant is either a dicotyledonous plant or a monocotyledonous plant. In another embodiment, the plant is further selected from the group consisting of an alfalfa, banana, barley, bean, broccoli, cabbage, *Brassica,* carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

In further embodiments, seeds comprising the recombinant nucleic acid molecules are disclosed.

In another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. In certain embodiments, the at least one other pesticidal agent is selected from the group consisting of an insect inhibitory protein, an insect inhibitory dsRNA molecule, and an ancillary protein. It is also contemplated that the at least one other pesticidal agent in the insect inhibitory composition exhibits activity against one or more pest species of the orders Lepidoptera, Coleoptera, or Hemiptera. The at least one other pesticidal agent in the insect inhibitory composition is in one embodiment selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC3131, TIC2160, VIP3A, VIP3B, VIP3Ab, AXMI-001, AXMI-002, AXMI-030, AXMI-035, AXMI-036, AXMI-045, Axmi52, Axmi58, Axmi88, Axmi97, Axmi102, Axmi112, Axmi117, Axmi100, AXMI-115, AXMI-113, and AXMI-005, AXMI134, AXMI-150, Axmi171, AXMI-184, axmi196, axmi204, axmi207, axmi209, Axmi205, AXMI218, AXMI220, AXMI221z, AXMI222z, AXMI223z, AXMI224z and AXMI225z, AXMI238, AXMI270, AXMI279, AXMI335, AXMI345, AXMI-R1, and variants thereof, IP3 and variants thereof, DIG-3, DIG-5, DIG-10, DIG-11, DIG-657 protein, PHI-4 variants, PIP-72 variants, PIP-45 variants, PIP-64 variants, PIP-74 variants, PIP-77 variants, DIG-305, PIP-47 variants, DIG-17, DIG-90, DIG-79, and DIG-303.

Commodity products comprising a detectable amount of the recombinant nucleic acid molecules disclosed in this application are also contemplated. Such commodity products include commodity corn bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including, where applicable, juices, concentrates, jams, jellies, marmalades, and other edible forms of such commodity products containing a detectable amount of such polynucleotides and or polypeptides of this application, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

Also contemplated in this application is a method of producing seed comprising the recombinant nucleic acid molecules disclosed in this application. The method comprises planting at least one of the seed comprising the recombinant nucleic acid molecules disclosed in this application; growing plant from the seed; and harvesting seed from the plants, wherein the harvested seed comprises the recombinant nucleic acid molecules in this application.

In another illustrative embodiment, a plant resistant to insect infestation, is provided wherein the cells of said plant comprise: (a) a recombinant nucleic acid molecule encoding an insecticidally effective amount of a pesticidal protein as set forth in SEQ ID NO:4, SEQ ID NO:2, SEQ ID NO:12, or SEQ ID NO:14; or (b) an insecticidally effective amount of a protein comprising an amino acid sequence having at least 80% or, 85%, or 90%, or 95%, or about 100% amino acid sequence identity to SEQ ID NO:4, SEQ ID NO:2, SEQ ID NO:12, or SEQ ID NO:14.

Also disclosed in this application are methods for controlling a Lepidopteran species pest, and controlling a Lepidopteran species pest infestation of a plant, particularly a crop plant. The method comprises, in one embodiment, (a) contacting the pest with an insecticidally effective amount of a pesticidal proteins as set forth in SEQ ID NO:4, SEQ ID NO:2, SEQ ID NO:12, or SEQ ID NO:14; or (b) contacting the pest with an insecticidally effective amount of one or more pesticidal proteins comprising an amino acid sequence having at least 80%, 85%, or 90%, or 95%, or about 100% amino acid sequence identity to identity to SEQ ID NO:4, SEQ ID NO:2, SEQ ID NO:12, or SEQ ID NO:14.

Further provided herein is a method of detecting the presence of a recombinant nucleic acid molecule comprising a polynucleotide segment encoding a pesticidal protein or fragment thereof, wherein: (a) said pesticidal protein comprises the amino acid sequence of SEQ ID NO:4, SEQ ID NO:2, SEQ ID NO:6; SEQ ID NO:8, SEQ ID NO:10, SEQ ID NO:12, or SEQ ID NO:14; or (b) said pesticidal protein comprises an amino acid sequence having at least 80%, or 85%, or 90%, or 95%, or 98%, or 99%, or about 100% amino acid sequence identity to SEQ ID NO:4, SEQ ID NO:2, SEQ ID NO:6; SEQ ID NO:8, SEQ ID NO:10, SEQ ID NO:12, or SEQ ID NO:14; or (c) said polynucleotide segment hybridizes to a polynucleotide having the nucleotide sequence of SEQ ID NO:3, SEQ ID NO:1, SEQ ID NO:5; SEQ ID NO:7, SEQ ID NO:9, SEQ ID NO:11, or SEQ ID NO:13. In one embodiment of the invention, the method comprises contacting a sample of nucleic acids with a nucleic acid probe that hybridizes under stringent hybridization conditions with genomic DNA from a plant comprising a polynucleotide segment encoding a pesticidal protein or fragment thereof provided herein, and does not hybridize under such hybridization conditions with genomic DNA from an otherwise isogenic plant that does not comprise the segment, wherein the probe is homologous or complementary to SEQ ID NO:3, SEQ ID NO:11, or SEQ ID NO:13, or a sequence that encodes a pesticidal protein comprising an amino acid sequence having at least 80%, or 85%, or 90%, or 95%, or 98%, or 99%, or about 100% amino acid sequence identity to SEQ ID NO:4, SEQ ID NO:2, SEQ ID NO:12, or SEQ ID NO:14. The method may further comprise (a) subjecting the sample and probe to stringent hybridization conditions; and (b) detecting hybridization of the probe with DNA of the sample.

Also provided by the invention are methods of detecting the presence of a pesticidal protein or fragment thereof in a sample comprising protein, wherein said pesticidal protein comprises the amino acid sequence of SEQ ID NO:4, SEQ ID NO:2, SEQ ID NO:6; SEQ ID NO:8, SEQ ID NO:10, SEQ ID NO:12, or SEQ ID NO:14; or said pesticidal protein comprises an amino acid sequence having at least 80%, or 85%, or 90%, or 95%, or 98%, or 99%, or about 100% amino acid sequence identity to SEQ ID NO:4, SEQ ID NO:2, SEQ ID NO:6; SEQ ID NO:8, SEQ ID NO:10, SEQ ID NO:12, or SEQ ID NO:14. In one embodiment, the method comprises: (a) contacting a sample with an immunoreactive antibody; and (b) detecting the presence of the protein. In some embodiments the step of detecting comprises an ELISA, or a Western blot.

Also disclosed in this application is a method for improving the insecticidal activity of a native insecticidal protein against an insect pest species, comprising: engineering a variant insecticidal protein by inserting a DNA fragment encoding an insect gut receptor binding peptide into a coding sequence encoding the insecticidal protein; wherein the insecticidal activity of the engineered insecticidal protein is greater than the insecticidal activity of the native insecticidal protein to said insect pest species. In one embodiment of the invention, the insect gut receptor can be a cadherin-like protein (CADR), a GPI-anchored aminopeptidase-N (APN), a GPI-anchored alkaline phosphatase, a transmembrane ABC transporter, or an ADAM metalloprotease. In another embodiment of the invention, the DNA fragment encoding an insect gut receptor binding peptide is selected from the group consisting of SEQ ID NO:15 and SEQ ID NO:16 and encodes the receptor binding peptide provided as SEQ ID NO:17.

In an embodiment of the invention are recombinant nucleic acid molecule comprising a heterologous promoter operably linked to a polynucleotide segment encoding a pesticidal protein or pesticidal fragment thereof, operably linked to a DNA sequence comprising a reproductive tissue-specific miRNA target binding site element, wherein said miRNA target binding site element is heterologous with respect to said polynucleotide segment encoding a pesticidal protein or pesticidal fragment thereof. The miRNA target binding site elements are selected from the group consisting of SEQ ID NO:18, SEQ ID NO:19, SEQ ID NO:20, SEQ ID NO:21, SEQ ID NO:22, and SEQ ID NO:23.

In yet another embodiment of the invention is a method for reducing expression of a pesticidal protein in the reproductive tissue of a transgenic plant, comprising expressing in said transgenic plant a recombinant nucleic acid molecule comprising a heterologous promoter operably linked to a polynucleotide segment encoding a pesticidal protein or pesticidal fragment thereof, operably linked to a DNA sequence comprising a reproductive tissue-specific miRNA target binding site element, wherein said miRNA target binding site element is heterologous with respect to said polynucleotide segment encoding a pesticidal protein or pesticidal fragment thereof. The miRNA target binding site elements are selected from the group consisting of SEQ ID NO:18, SEQ ID NO:19, SEQ ID NO:20, SEQ ID NO:21, SEQ ID NO:22, and SEQ ID NO:23. A further embodiment of the invention is a recombinant DNA molecule selected from the group consisting of SEQ ID NO:25 and SEQ ID NO:26.

BRIEF DESCRIPTION OF THE SEQUENCES

SEQ ID NO:1 is a nucleic acid sequence encoding a TIC7941 pesticidal protein obtained from *Paenibacillus lentimorbus* species DSC020651.

SEQ ID NO:2 is the amino acid sequence of the TIC7941 pesticidal protein.

SEQ ID NO:3 is a synthetic coding sequence encoding a TIC7941PL_1 pesticidal protein designed for expression in a plant cell.

SEQ ID NO:4 is the amino acid sequence of the TIC7941PL_1 protein wherein an additional alanine amino acid is inserted immediately following the initiating methionine.

SEQ ID NO:5 is a nucleic acid sequence encoding a TIC7941_His pesticidal protein, wherein a nucleic acid sequence encoding a Histidine tag is operably linked 5' and in frame to the TIC7941 coding sequence.

SEQ ID NO:6 is the amino acid sequence of the TIC7941_His pesticidal protein.

SEQ ID NO:7 is a nucleic acid sequence encoding a TIC7941_2His pesticidal protein, wherein a nucleic acid sequence encoding a Histidine tag is operably linked 5' and in frame.

SEQ ID NO:8 is the amino acid sequence of the TIC7941_2His pesticidal protein.

SEQ ID NO:9 is a nucleic acid sequence encoding a TIC7941_3His pesticidal protein, wherein a nucleic acid sequence encoding a Histidine tag is operably linked 5' and in frame.

SEQ ID NO:10 is the amino acid sequence of the TIC7941_3His pesticidal protein.

SEQ ID NO:11 is a synthetic coding sequence encoding a TIC7941PL_2 pesticidal protein designed for expression in a plant cell.

SEQ ID NO:12 is the amino acid sequence of TIC7941PL_2 wherein an additional alanine amino acid is inserted immediately following the initiating methionine.

SEQ ID NO:13 is a synthetic coding sequence encoding a TIC7941PL_3 pesticidal protein designed for expression in a plant cell.

SEQ ID NO:14 is the amino acid sequence of TIC7941PL_3 wherein an additional alanine amino acid is inserted immediately following the initiating methionine.

SEQ ID NO:15 is a synthetic coding sequence (FAW-PEPBIN_Bac) encoding the FAW ABCc4 receptor binding peptide sequence FAWPEPBIN for expression in bacteria. The synthetic sequence is found within nucleotide positions 2413-2448 of TIC7941_2His and within nucleotide positions 2410-2445 of TIC7941_3His.

SEQ ID NO:16 is a synthetic coding sequence (FAW-PEPBIN_PL) encoding the FAW ABCc4 receptor binding peptide sequence FAWPEPBIN for expression in a plant cell. The synthetic sequence is found within nucleotide positions 2386-2421 of TIC7941PL_2 and within nucleotide positions 2383-2418 of TIC7941PL_3.

SEQ ID NO:17 is the FAW ABCc4 receptor binding peptide sequence (FAWPEPBIN) encoded by SEQ ID NO:15 and SEQ ID NO:16 and is located at amino acid positions 805-816 of TIC7941_2His, 804-815 of TIC7941_3His, 796-807 of TIC7941PL_2, and 795-806 of TIC7941PL_3.

SEQ ID NO:18 is a DNA sequence encoding an miRNA target binding site Gm.miR395_1.

SEQ ID NO:19 is a DNA sequence encoding an miRNA binding target site Gm.miR395_2.

SEQ ID NO:20 is a DNA sequence (SUP-miR395) wherein the miRNA target binding sites Gm.miR395_1 and Gm.miR395_2 are linked using a DNA sequence SP-ART.8a-1.

SEQ ID NO:21 is a DNA sequence encoding an miRNA target binding site Gm.miR4392_1.

SEQ ID NO:22 is a DNA sequence encoding an miRNA target binding site Gm.miR4392_2.

SEQ ID NO:23 is a DNA sequence (SUP-miR4392) wherein the miRNA target binding sites Gm.miR4392_1 and Gm.miR4392_2 are linked using a DNA sequence SP-ART.8a-1.

SEQ ID NO:24 is the DNA sequence of the linker SP-ART.8a-1.

SEQ ID NO:25 is a DNA sequence (TIC7941PL_1-mi395) encoding TIC7941PL_1 operably linked to SUP-miR395.

SEQ ID NO:26 is a DNA sequence (TIC7941PL_1-mi4392) encoding TIC7941PL_1 operably linked to SUP-miR4392.

DETAILED DESCRIPTION OF THE INVENTION

The problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

Novel pesticidal proteins exemplified by TIC7941, TIC7941PL_1, TIC7941PL_2, and TIC7941PL_3 are disclosed herein, and address each of these needs, particularly against a broad spectrum of Lepidopteran insect pests, and more particularly against Black cutworm (*Agrotis ipsilon*), Corn earworm (*Helicoverpa zea*), European corn borer (*Ostrinia nubilalis*), Fall armyworm (*Spodoptera frugiperda*), Southern armyworm (*Spodoptera eridania*), Soybean looper (*Chrysodeixis includens*), Southwestern corn borer (*Diatraea grandiosella*).

Reference in this application to TIC7941, "TIC7941 protein", "TIC7941 protein toxin", "TIC7941 toxin protein", "TIC7941 pesticidal protein", "TIC7941-related toxins", "TIC7941-related toxin proteins", TIC7941PL_1, "TIC7941PL_1 protein", "TIC7941PL_1 protein toxin", "TIC7941PL_1 toxin protein", "TIC7941PL_1 pesticidal protein", "TIC7941PL_1-related toxins", "TIC7941PL_1-related toxin proteins", and the like, refer to any novel pesticidal protein or insect inhibitory protein, that comprises, that consists of, that is substantially homologous to, that is similar to, or that is derived from any pesticidal protein or insect inhibitory protein sequence of TIC7941 (SEQ ID NO:2), TIC7941PL_1 (SEQ ID NO:4), TIC7941PL_2 (SEQ ID NO:12), and TIC7941PL_3 (SEQ ID NO:14) and pesticidal or insect inhibitory segments thereof, or combinations thereof, that confer activity against Lepidopteran pests, including any protein exhibiting pesticidal or insect inhibitory activity if alignment of such protein with TIC7941, TIC7941PL_1, TIC7941PL_2, or TIC7941PL_3 results in amino acid sequence identity of any fraction percentage form about 80% to about 100% percent. The TIC7941, TIC7941PL_1, TIC7941PL_2, and TIC7941PL_3 proteins include both the plastid-targeted and non-plastid targeted form of the proteins.

The term "segment" or "fragment" is used in this application to describe consecutive amino acid or nucleic acid sequences that are shorter than the complete amino acid or nucleic acid sequence describing a TIC7941 protein. A segment or fragment exhibiting insect inhibitory activity is also disclosed in this application if alignment of such segment or fragment, with the corresponding section of the TIC7941 protein set forth in SEQ ID NO:2, or TIC7941PL_1 protein set forth in SEQ ID NO:4, or TIC7941PL_2 protein set forth in SEQ ID NO:12, or TIC7941PL_3 protein set forth as SEQ ID NO:14 results in amino acid sequence identity of any fraction percentage from about 80 to about 100 percent between the segment or fragment and the corresponding section of the TIC7941, TIC7941PL_1, TIC7941PL_2, or TIC7941PL_3 protein.

In still further specific embodiments, a fragment of a TIC7941, TIC7941PL_1, TIC7941PL_2, or TIC7941PL_3 protein may be defined as exhibiting pesticidal activity possessed by the starting protein molecule from which it is derived. A fragment of a nucleic acid sequence encoding a TIC7941, TIC7941PL_1, TIC7941PL_2, or TIC7941PL_3 protein may be defined as encoding a protein exhibiting the pesticidal activity possessed by the protein molecule encoded by the starting nucleic acid sequence from which it is derived. A fragment or variant described herein may further comprise a domain identified herein which is responsible for the pesticidal activity of a protein.

In specific embodiments, fragments of a TIC7941, TIC7941PL_1, TIC7941PL_2, or TIC7941PL_3 protein are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, at least about 1000, at least about 1100, at least about 1150, or at least about 1175 contiguous amino acids, or longer, of a TIC7941, TIC7941PL_1, TIC7941PL_2, or TIC7941PL_3 protein having pesticidal activity as disclosed herein. In certain embodiments, the invention provides fragments of any one of SEQ ID NOs: 2, 4, 12, or 14, having the activity of the full length sequence. Methods for producing such fragments from a starting molecule are well known in the art.

Reference in this application to the terms "active" or "activity", "pesticidal activity" or "pesticidal" or "insecticidal activity", "insect inhibitory" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the TIC7941 protein) or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents and pesticidal or insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Lepidopterans, as well as protein toxins that are used to control other plant pests such as Cry and Cyt proteins available in the art for use in controlling Coleopteran, Hemipteran and Homopteran species.

It is intended that reference to a pest, particularly a pest of a crop plant, means insect pests of crop plants, particularly those Lepidoptera insect pests that are controlled by the TIC7941 protein toxin class. However, reference to a pest can also include Coleopteran, Hemipteran and Homopteran insect pests of plants, as well as nematodes and fungi when toxic agents targeting these pests are co-localized or present together with the TIC7941 protein or a protein that is 80 to about 100 percent identical to TIC7941protein.

The TIC7941 proteins are related by a common function and exhibit insecticidal activity towards insect pests from the Lepidoptera insect species, including adults, pupae, larvae, and neonates.

The insects of the order Lepidoptera include, but are not limited to, armyworms, cutworms, loopers, and heliothines in the Family Noctuidae, e.g., Fall armyworm (*Spodoptera frugiperda*), Beet armyworm (*Spodoptera exigua*), Black armyworm (*Spodoptera exempta*), Southern armyworm (*Spodoptera eridania*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*), and gypsy moth (*Lymantria dispar*). Other insect pests of order Lepidoptera include, e.g., cotton leaf worm (*Alabama argillacea*), fruit tree leaf roller (*Archips argyrospila*), European leafroller (*Archips rosana*) and other Archips species, (*Chilo suppressalis,* Asiatic rice borer, or rice stem borer), rice leaf roller (*Cnaphalocrocis medinalis*), corn root webworm (*Crambus caliginosellus*), bluegrass webworm (*Crambus teterrellus*), southwestern corn borer (*Diatraea grandiosella*), surgarcane borer (*Diatraea saccharalis*), spiny bollworm (*Earias insulana*), spotted bollworm (*Earias vittella*), American bollworm (*Helicoverpa armigera*), corn earworm (*Helicoverpa zea,* also known as soybean podworm and cotton bollworm), tobacco budworm (*Heliothis virescens*), sod webworm (*Herpetogramma licarsisalis*), Western bean cutworm (*Striacosta albicosta*), European grape vine moth (*Lobesia botrana*), citrus leafminer (*Phyllocnistis citrella*), large white butterfly (*Pieris brassicae*), small white butterfly (*Pieris rapae,* also known as imported cabbageworm), beet armyworm (*Spodoptera exigua*), tobacco cutworm (*Spodoptera litura,* also known as cluster caterpillar), and tomato leafminer (*Tuta absoluta*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation or gene editing. Similarly, a "recombinant protein molecule" is a protein molecule comprising a combination of amino acids that would not naturally occur together without human intervention. For example, a recombinant protein molecule may be a protein molecule that is comprised of at least two amino acid molecules heterologous with respect to each other, a protein molecule that comprises an amino acid sequence that deviates from amino acid sequences that exist in nature, or a protein molecule that is expressed in a host cell as a result of genetic transformation of the host cell or by gene editing of the host cell genome.

As described further in this application, an open reading frame (ORF) encoding TIC7941 (SEQ ID NO:2) was discovered in DNA obtained from *Paenibacillus lentimorbus* strain DSC020651. The coding sequence was cloned and expressed in microbial host cells to produce recombinant proteins used in bioassays. Bioassay using microbial host cell-derived proteins of TIC7941 demonstrated activity against the Lepidopteran species Black cutworm (*Agrotis ipsilon*), Corn earworm (*Helicoverpa zea*), European corn borer (*Ostrinia nubilalis*), Southern armyworm (*Spodoptera eridania*), Soybean looper (*Chrysodeixis includens*), and Southwestern corn borer (*Diatraea grandiosella*).

Synthetic sequences encoding TIC7941 and variants of TIC7941 were designed for expression in a plant cell. The coding sequence, TIC7941PL_1 (SEQ ID NO:3) encodes the TIC7941PL_1 insecticidal protein which is identical to the TIC7941 protein sequence with the exception of an additional alanine amino acid inserted after the initiating methionine to improve expression. When expressed in transgenic corn, TIC7941PL_1 demonstrated insecticidal activity against Black cutworm (BCW, *Agrotis ipsilon*), Corn earworm (CEW, *Helicoverpa zea*), and Southwestern corn borer (SWCB, *Diatraea grandiosella*) in leaf disc assays. When expressed in transgenic soybean plants, TIC7941PL_1 demonstrates insecticidal activity against Southern armyworm (SAW, *Spodoptera eridania*), Soybean looper (SBL, *Chrysodeixis includens*), and Soybean podworm (SPW, *Helicoverpa zea*) in leaf disc assays. The TIC7941PL_2 coding sequence (SEQ ID NO:11) and TIC7941PL_3 coding sequence (SEQ ID NO:13) encode the TIC7941PL_2 (SEQ ID NO:12) and TIC7941PL_3 (SEQ ID NO:14) insecticidal proteins, respectively. They contain an additional alanine amino acid inserted after the initiating methionine to improve expression. Both TIC7941PL_2 and TIC7941PL_3 also contain a Fall armyworm transmembrane ABC transporter (ABCc4) protein binding peptide fragment inserted within the domain 2 loop of TIC7941. In TIC7941PL_2 the ABCc4 protein binding fragment is located at amino acid positions 796-807. In TIC7941PL_3 the ABCc4 protein binding fragment is located at amino acid positions 795-806.

For expression in plant cells, the TIC7941PL_1, TIC7941PL_2, or TIC7941PL_3 protein can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the TIC7941, TIC7941PL_1, TIC7941PL_2, or TIC7941PL_3 toxin protein to the chloroplast, a sequence encoding a chloroplast transit peptide is placed 5' in operable linkage and in frame to a synthetic coding sequence encoding the TIC7941, TIC7941PL_1, TIC7941PL_2, or TIC7941PL_3 toxin protein that has been designed for optimal expression in plant cells.

It is contemplated that additional toxin protein sequences related to TIC7941 can be created by using the amino acid sequence of TIC7941 to create novel proteins with novel properties. The TIC7941 toxin proteins can be aligned to combine differences at the amino acid sequence level into novel amino acid sequence variants and making appropriate changes to the recombinant nucleic acid sequence encoding the variants.

This disclosure further contemplates that improved variants of the TIC7941 protein toxin class can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence is altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

It is also contemplated that fragments of TIC7941 or protein variants thereof can be truncated forms wherein one or more amino acids are deleted from the N-terminal end, C-terminal end, the middle of the protein, or combinations thereof wherein the fragments and variants retain insect inhibitory activity. These fragments can be naturally occurring or synthetic variants of TIC7941 or derived protein variants, but should retain the insect inhibitory activity of at least TIC7941. A fragment or variant described herein may further comprise a domain identified herein which is responsible for the pesticidal activity of a protein.

Proteins that resemble the proteins in the TIC7941 protein toxin class can be identified and compared to each other using various computer based algorithms known in the art (see Table 1) Amino acid sequence identities reported in this application are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment and are contemplated herein.

It is intended that a protein exhibiting insect inhibitory activity against a Lepidopteran insect species is related to a member of the TIC7941 protein toxin class if the protein is used in a query, e.g., in a Clustal W alignment, and the proteins of the present invention as set forth as SEQ ID NO:2, SEQ ID NO:4, SEQ ID NO:8, or SEQ ID NO:10 are identified as hits in such alignment in which the query protein exhibits at least 80% to about 100% amino acid identity along the length of the query protein that is about 80%, 81%, 82%, 83%, 84%, 85%, 86%, 87%, 88%, 89%, 90%, 91%, 92%, 93%, 94%, 95%, 96%, 97%, 98%, 99%, 100%, or any fraction percentage in this range.

In addition to percent identity, TIC7941 proteins can also be related by primary structure (conserved amino acid motifs), by length (about 807 amino acids), and by other characteristics. Characteristics of the TIC7941 protein toxins are reported in Table 1.

TABLE 1

Selected characteristics of the TIC7941 protein toxin class.

| Protein | Molecular Weight (in Daltons) | Amino Acid Length | Isoelectric Point | Charge at PH 7.0 | No. of Strongly Basic (−) Amino Acids | No. of Strongly Acidic Amino Acids | No. of Hydrophobic Amino Acids | No. of Polar Amino Acids |
|---|---|---|---|---|---|---|---|---|
| TIC7941 | 91187.48 | 807 | 4.4561 | −35.5 | 87 | 118 | 394 | 413 |
| TIC7941PL_1 | 91258.56 | 808 | 4.4561 | −35.5 | 87 | 118 | 395 | 413 |
| TIC7941PL_2 | 92245.74 | 817 | 4.4414 | −36.5 | 87 | 119 | 402 | 415 |
| TIC7941PL_3 | 92203.70 | 817 | 4.4544 | −35.5 | 87 | 118 | 402 | 415 |

As described further in the Examples, synthetic nucleic acid molecule sequences encoding variants of TIC7941 were designed for use in plants. Exemplary recombinant nucleic acid molecule sequences that were designed for use in plants encoding the TIC7941PL_1, TIC7941PL_2, and TIC7941PL_3 proteins are presented as SEQ ID NO:3, SEQ ID NO:11, and SEQ ID NO:13, respectively. The TIC7941PL_1, TIC7941PL_2, and TIC7941PL_3 proteins have an additional alanine amino acid immediately following the initiating methionine relative to the TIC7941 protein. This additional alanine residue is believed to improve expression of the protein in planta. The TIC7941PL_2 and TIC7941PL_3 proteins also comprise the ABCc4 peptide binding fragment to improve efficacy of the proteins against Fall armyworm (*Spodoptera frugiperda*).

Expression cassettes and vectors containing a recombinant nucleic acid molecule sequence can be constructed and introduced into corn, soybean or cotton plant cells in accordance with transformation methods and techniques known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257A1 (sugar beet), U.S. Pat. No. 5,750,871 (canola), U.S. Pat. No. 7,026,528 (wheat), and U.S. Pat. No. 6,365,807 (rice), and in Arencibia et al. (1998) Transgenic Res. 7:213-222 (sugarcane) all of which are incorporated herein by reference in their entirety. Transformed cells can be regenerated into transformed plants that express TIC7941PL_1, TIC7941PL_2, or TIC7941PL_3 protein and demonstrate pesticidal activity through bioassays performed in the presence of Lepidopteran pest larvae using plant leaf disks obtained from the transformed plants. Plants can be derived from the plant cells by regeneration, seed, pollen, or meristem transformation techniques. Methods for transforming plants are known in the art.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. Briefly as understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

Recombinant nucleic acid molecule compositions that encode TIC7941 proteins are contemplated. For example, TIC7941, TIC7941PL_1, TIC7941PL_2, and TIC7941PL_3 proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to a TIC7941 protein encoding sequence for expression of the protein in plants or a Bt-functional promoter operably linked to a TIC7941 protein encoding sequence for expression of the protein in a Bt bacterium or other *Bacillus* species. Other elements can be operably linked to the TIC7941 protein encoding sequence including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NO:3, SEQ ID NO:1, SEQ ID NO:5, SEQ ID NO:7, SEQ ID NO:9, SEQ ID NO:11, and SEQ ID NO:13 that encodes the respective polypeptides or proteins having the amino acid sequence as set forth in SEQ ID NO:4, SEQ ID NO:2, SEQ ID NO:6, SEQ ID NO:8, SEQ ID NO:10, SEQ ID NO:12, and SEQ ID NO:14. A heterologous promoter can also be operably linked to synthetic DNA coding sequences encoding a plastid targeted TIC7941PL_1, TIC7941PL_2, or TIC7941PL_3 or an untargeted TIC7941PL_1, TIC7941PL_2, or TIC7941PL_3. The codons of a recombinant nucleic acid molecule encoding for proteins disclosed herein can be substituted by synonymous codons (known in the art as a silent substitution).

A recombinant DNA construct comprising a TIC7941 protein encoding sequence can further comprise a region of DNA that encodes for one or more insect inhibitory agents which can be configured to concomitantly express or co-express with a DNA sequence encoding a TIC7941 protein, a protein different from a TIC7941 protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecules is under separate promoter control or some combination thereof. The proteins of this invention can be expressed from a multi-gene expression system in which one or more proteins of the TIC7941 protein toxin class are expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked or linked expression cassettes, each cassette expressing a different protein or other agent such as one or more dsRNA molecules.

Recombinant polynucleotides or recombinant DNA constructs comprising a TIC7941 protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC7941 protein encoding sequence in a host cell, or subsequent expression of the encoded polypeptide. An exogenous recombinant polynucleotide or recombinant DNA construct that comprises a TIC7941 protein encoding sequence and that is introduced into a host cell is referred in this application as a "transgene".

Transgenic bacteria, transgenic plant cells, transgenic plants, and transgenic plant parts that contain a recombinant polynucleotide that expresses TIC7941, TIC7941_His, TIC7941PL_1, TIC7941PL_2, or TIC7941PL_3 protein encoding sequence is provided herein. The term "bacterial cell" or "bacterium" can include, but is not limited to, an *Agrobacterium,* a *Bacillus,* an *Escherichia,* a *Salmonella,* a *Pseudomonas,* a *Brevibacillus,* a *Klebsiella,* an *Erwinia,* or a *Rhizobium* cell. The term "plant cell" or "plant" can include but is not limited to a dicotyledonous or monocotyledonous plant. The term "plant cell" or "plant" can also include but is not limited to an alfalfa, banana, barley, bean, broccoli, cabbage, *Brassica,* carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Lepidoptera-inhibitory amounts of a TIC7941 protein are provided. Such plants can be made by introducing a recombinant polynucleotide that encodes any of the proteins provided in this application into a plant cell, and selecting a plant derived from said plant cell that expresses an insect, Lepidoptera-inhibitory amount of the proteins. Plants can be derived from the plant cells by regeneration, seed, pollen, or meristem transformation techniques. Methods for transforming plants are known in the art.

Processed plant products, wherein the processed product comprises a detectable amount of a TIC7941 protein, an insect inhibitory segment or fragment thereof, or any distinguishing portion thereof, are also disclosed herein. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC7941 protein.

Plants expressing a TIC7941 protein can be crossed by breeding with transgenic events expressing other toxin proteins and/or expressing other transgenic traits such as herbicide tolerance genes, genes conferring yield or stress tolerance traits, and the like, or such traits can be combined in a single vector so that the traits are all linked.

As further described in the Examples, the TIC7941 protein toxin class and sequences having a substantial percentage identity to a member of the TIC7941 protein toxin class can be identified using methods known to those of ordinary skill in the art such as polymerase chain reaction (PCR), thermal amplification and hybridization. For example, the proteins in the TIC7941 protein toxin class can be used to produce antibodies that bind specifically to related proteins, and can be used to screen for and to find other protein members that are closely related.

Furthermore, nucleotide sequences encoding the TIC7941 toxin proteins can be used as probes and primers for screening to identify other members of the class using thermal-cycle or isothermal amplification and hybridization methods. For example, oligonucleotides derived from sequences as set forth in SEQ ID NO:3, SEQ ID NO:11, and SEQ ID NO:13 can be used to determine the presence or absence of a TIC7941 transgene in a deoxyribonucleic acid sample derived from a commodity product. Given the sensitivity of certain nucleic acid detection methods that employ oligonucleotides, it is anticipated that oligonucleotides derived from sequences as set forth in SEQ ID NO:3, SEQ ID NO:11, and SEQ ID NO:13 can be used to detect a TIC7941PL_1, TIC7941PL_2, and TIC7941PL_3 transgene in commodity products derived from pooled sources where only a fraction of the commodity product is derived from a transgenic plant containing any of the transgenes. It is further recognized that such oligonucleotides can be used to introduce nucleotide sequence variation in each of SEQ ID NO:3, SEQ ID NO:11, and SEQ ID NO:13. Such "mutagenesis" oligonucleotides are useful for identification of TIC7941 protein toxin class amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under stringent hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes to the second nucleotide sequence. In such case, the second nucleotide sequence can be any of the nucleotide sequences presented as SEQ ID NO:3, SEQ ID NO:1, SEQ ID NO:11, and SEQ ID NO:13 under stringent hybridization conditions. Nucleotide coding sequences hybridize to one another under appropriate hybridization conditions, such as stringent hybridization conditions, and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding such related proteins, and those sequences, to the extent that they function to express pesticidal proteins either in Bacillus strains or in plant cells, are embodiments of the present invention, recognizing of course that many such redundant coding sequences will not hybridize under these conditions to the native Bacillus or Paenibacillus sequences encoding TIC7941. This application contemplates the use of these and other identification methods known to those of ordinary skill in the art to identify TIC7941 protein-encoding sequences and sequences having a substantial percentage identity to TIC7941 protein-encoding sequences.

This disclosure also contemplates the use of molecular methods known in the art to engineer and clone commercially useful proteins comprising chimeras of proteins from pesticidal proteins; e.g., the chimeras may be assembled from segments of the TIC7941-related proteins to derive additional useful embodiments including assembly of segments of TIC7941, TIC7941PL_1, TIC7941PL_2, and TIC7941PL_3 with segments of diverse proteins different from TIC7941, TIC7941PL_1, TIC7941PL_2, and TIC7941PL_3; and related proteins. The TIC7941 proteins may be subjected to alignment to each other and to other Bacillus, Paenibacillus or other pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

In addition, this disclosure contemplates engineering a variant pesticidal protein by inserting peptide sequences within the native pesticidal protein that can improve the pesticidal activity against specific insect pest species. The inserted peptide binds to an insect midgut receptor. Specific binding of the endotoxin to specific receptors located in the insect midgut is one step in the mode of pesticidal action of a pesticidal protein. At least five different protein receptors have been described to be involved in interactions leading to insect mortality: a cadherin-like protein (CADR), a glycosylphosphatidyl-inositol (GPI)-anchored aminopeptidase-N (APN), a GPI-anchored alkaline phosphatase (ALP), a transmembrane ABC transporter, and an "A Disentegrin And Metalloprotease" or ADAM metalloprotease. In addition, it has been proposed that glycolipids are also important Cry-receptor molecules in insects and nematodes (Pigott et al. (2007) *Role of Receptors in Bacillus thuringiensis Crystal Toxin Activity. Microbiology and Molecular Biology Reviews*, 71(2): 255-281; Ochoa-Campuzano et al. (2007) *An ADAM metalloprotease is a Cry3Aa Bacillus thuringiensis toxin receptor. Biochemical and Biophysical Research Communication*, 362(2): 437-442). The peptide fragment, FAWPEPBIN binds to the Fall Armyworm (FAW) transmembrane ABC transporter ABCc4. Insertion of the coding sequence, FAWPEPBIN_Bac (SEQ ID NO:15), encoding the peptide FAWPEPBIN (SEQ ID NO:17) within the domain 2 loop of TIC7941 increased pesticidal activity against FAW in certain variants. Specifically, insertion of FAWPEPBIN in amino acid positions 805-816 in TIC7941_2His resulted in little or no demonstrated activity against FAW whereas insertion of FAWPEPBIN in amino acid positions 804-815 of TIC7941_3His demonstrated activity against FAW.

A synthetic DNA sequence encoding the FAWPEPBIN peptide, FAWPEPBIN_PL, (SEQ ID NO:16) was designed for expression in a plant cell. FAWPEPBIN_PL is found between nucleotide positions 2386 and 2421 of the synthetic coding sequence TIC7941PL_2 and within nucleotide positions 2383-2418 of the TIC7941PL_3 synthetic coding sequence. The FAWPEPBIN peptide fragment is located within amino acid positions 796-807 of TIC7941PL_2 and 795-806 of TIC7941PL_3. Corn plants were transformed with binary vectors comprising transgene cassettes used for the expression of TIC7941PL_2 and TIC7941PL_3. The plants expressing TIC7941PL_2 and TIC7941PL_3 will be used to assay the pesticidal activity of the engineered toxins against FAW.

Methods of controlling insects, in particular Lepidoptera infestations of crop plants, with the TIC7941 proteins are also disclosed in this application. Such methods can comprise growing a plant comprising an insect- or Lepidoptera-inhibitory amount of a TIC7941 toxin protein. In certain embodiments, such methods can further comprise any one or more of: (i) applying any composition comprising or encoding a TIC7941 toxin protein to a plant or a seed that gives rise to a plant; and (ii) transforming a plant or a plant cell that gives rise to a plant with a polynucleotide encoding a TIC7941 toxin protein. In general, it is contemplated that a TIC7941 toxin protein can be provided in a composition, provided in a microorganism, or provided in a transgenic plant to confer insect inhibitory activity against Lepidopteran insects.

In certain embodiments, a recombinant nucleic acid molecule of a TIC7941 toxin protein is the pesticidally active ingredient of an insect inhibitory composition prepared by culturing recombinant *Bacillus* or any other recombinant bacterial cell transformed to express a TIC7941 toxin protein under conditions suitable to express the TIC7941 toxin protein. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising a TIC7941 toxin protein can further comprise at least one additional polypeptide that exhibits insect inhibitory activity against the same Lepidopteran insect species, but which is different from the TIC7941 toxin protein. Possible additional polypeptides for such a composition include any insect inhibitory protein or insect inhibitory dsRNA molecule known to a person of ordinary skill in the art. One example for the use of such ribonucleotide sequences to control insect pests is described in Baum, et al. (U.S. Patent Publication 2006/0021087 A1). Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. Patent Publication No. 10/525,318), Cry1C (U.S. Pat. No. 6,033,874), Cry1D, Cry1Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869, and TIC1100 (International Application Publication WO2016/061391 (A2)), TIC2160 (International Application Publication WO2016/061392(A2)), Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523(A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), DIG-657 (International Application Publication WO2015/195594 A2), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1), DIG-911 and DIG-180 as described in US Patent Publication No. 2015-0264940A1; and the like.

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Hemipteran pests, combinations of insect inhibitory proteins of the present invention can be used with Hemipteran-active proteins such as TIC1415 (US Patent Publication 2013-0097735 A1), TIC807 (U.S. Pat. No. 8609936), TIC834 (U.S. Patent Publication 2013-0269060 A1), AXMI-036 (U.S. Patent Publication 2010-0137216 A1), and AXMI-171 (U.S. Patent Publication 2013-0055469 A1). Further a polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), AXMI-207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1), PHI-4 variants (U.S. Patent Application Publication 2016-0281105 A1), PIP-72 variants (WO 2016-144688 A1), PIP-45 variants, PIP-64 variants, PIP-74 variants, PIP-75 variants, and PIP-77 variants (WO 2016-144686 A1), DIG-305 (WO 2016109214 A1), PIP-47 variants (U.S. Patent Publication 2016-0186204 A1), DIG-17, DIG-90, DIG-79 (WO 2016-057123 A1), DIG-303 (WO 2016-070079 A1), and $\overline{\omega}$ -Hexatoxin-Hv1a (U.S. Patent Application Publication US2014-0366227 A1).

Additional polypeptides for the control of Coleopteran, Lepidopteran, and Hemipteran insect pests can be found on the *Bacillus thuringiensis* toxin nomenclature website maintained by Neil Crickmore (accessible on the internet at www.btnomenclature.info).

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC7941 pesticidal proteins.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or pesticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

This disclosure also contemplates compositions and methods for reducing expression of a pesticidal protein in the reproductive tissues of a transgenic plant through the use of microRNAs (miRNAs). miRNAs are essential components of the gene silencing machinery in plants. In plants, the production of miRNAs is a tissue-specific process, is tightly associated with transcription and splicing, and even varies between miRNA precursors. Encoded by nuclear DNA in plants, miRNAs function via base-pairing with complementary sequences within mRNA molecules (Achkar et al. (2016) *miRNA Biogenesis: A Dynamic Pathway, Trends in Plant Science.* 21(12): 1034-1044). miRNAs are produced from a primary miRNA transcript (pri-miRNA). The nascent pri-miRNAs are capped at the 5' end and polyadenylated at the 3' end, and intron-containing pri-miRNAs are spliced or alternatively spliced. pri-miRNAs are processed by the dicing complex which contains the nuclear RNase DICER-LIKE 1 (DCL1) and its accessory proteins SERRATE (SE) and HYPONASTIC LEAVES (HYL1) as core components, to yield mature twenty-one (21) nucleotide miRNA/miRNA* duplexes. The miRNA/miRNA* duplex is stabilized through 3'-terminal 2'-O-methylation by HUA ENA-HANCER 1 (HEN1). HEN1 also contributes to export of the miRNA/miRNA* duplex from the cell nucleus and RNA-induced silencing complex (RISC) assembly. During RICS loading, one strand of the small RNA duplex is selected as the guide strand and incorporated into ARGONAUTE 1 (AGO1) to form a functional RISC, whereas the other strand (the passenger strand) is removed and degraded. The loading of miRNAs into AGO proteins is affected by the bulges in the miRNA/miRNA* duplexes caused by base pair mismatches. AGO1 prefers duplexes with central mismatches (Yu et al. (2017) *The "how" and "where" of plant microRNAs. New Phytologist,* 216: 1002-1017).

Plant miRNAs regulate target genes at the post-transcriptional level via two major mechanisms: transcript cleavage and translation repression. In plants, translation repression is less frequently observed than transcript cleavage. miRNA-guided RNA cleavage occurs at a precise position in the target mRNA. Cleavage is accomplished by the PIWI domain of AGO proteins, which forms an RNase H-like fold and exhibits endonuclease activity. The 5' and 3' cleavage fragments are subsequently degraded by exonucleases. Known factors required for miRNA-mediated translation inhibition include the microtubule-severing enzyme KATANIN 1 (KTN1), the processing body (P body) component of VARICOSE (VCS), the GW-repeat protein SUO, and the ER membrane protein ALTERED MERISTEM PROGRAM 1 (AMP1). Mutations in these genes selectively interfere with miRNA-guided repression at the protein level, suggesting that transcript cleavage and translation repression are two independent modes of action. The molecular mechanism underlying miRNA-mediated translation repression is not well understood. In vitro analysis suggests that plant miRNAs could inhibit translation initiation or hinder the movement of ribosomes (Yu et al. (2017) *The "how" and "where" of plant microRNAs. New Phytologist,* 216: 1002-1017).

In addition to mRNA cleavage and translation repression, some miRNAs also trigger the production of secondary short interfering RNAs (siRNAs) from their transcripts, and this is a widespread and conserved phenomenon in plants (Yu et al. (2017) *The "how" and "where" of plant microRNAs. New Phytologist,* 216: 1002-1017). The miRNAs that typically trigger the production of these secondary siRNAs are twenty-two (22) nucleotides in length as opposed to the twenty-one (21) nucleotide miRNAs described above. The targeted RNA is converted into double-stranded RNA (dsRNA) by RNA-dependent RNA polymerase (RdRp), which is then cleaved into siRNAs by DCL nucleases. Typically, one strand of the duplex preferentially associates with an AGO protein to form an effector complex (RNA-induced silencing complex, or RISC), that targets and silences transcripts based on sequence complementarity. In *Arabidopsis,* after *AGO*1-mediated miRNA-guided RNA cleavage of the target RNA, either the 5' or 3' cleavage fragment is stabilized by SUPPRESSOR OF GENE SILENCING 3 (SGS3), which associates with RISC by recognizing features of the twenty-two (22) nucleotide miRNA/target duplex to protect the cleavage. RNA-DEPENDENT RNA POLYMERASE 6 (RDR6) is recruited to convert the cleavage fragment into dsRNA which is later diced into siRNAs at a twenty-one (21) nucleotide interval fragment from degradation. In plants, this process can be amplified through production of secondary siRNAs after transcription by RNA-dependent RNA polymerase (RdRp) on the primary target RNA. (Cuperus et al., (2010) *Unique Functionality of 22 nt miRNAs in Triggering RDR6-Dependent siRNA Biogenesis from Target Transcripts in Arabidopsis. Nat Struct Mol Biol,* 17(8): 997-1003; Chen et al., (2010) 22-*Nucleotide RNAs trigger secondary siRNA biogenesis in Plants. Proceedings of the National Academy of Sciences,* 107: 15269-15274; Yu et al. (2017) *The "how" and "where" of plant microRNAs. New Phytologist,* 216: 1002-1017).

Through data mining of miRNAs in various tissues in soybean, two miRNAs were identified that were over-represented in reproductive tissues when compared to vegetative tissues; miR395 and miR4392. miR395 is processed into a twenty-one (21) nucleotide miRNA/miRNA* duplex and is expressed mostly in the soybean flower stamen. miR4392 is processed into a twenty-two (22) nucleotide miRNA/miRNA* duplex and triggers the production of secondary siRNAs from its transcripts, amplifying the suppression signal. miR4392 is highly enriched in the soybean flower anthers. Bound with an ARGO protein to form a silencing complex, miRNAs function as sequence-specific guides, directing the silencing complex to transcripts through base pairing between the miRNA and complementary sites herein referred to as "miRNA target binding sites", within the 3' untranslated region (3' UTR) of the target RNAs. miRNA target binding sites corresponding to miR395 (Gm.miR395_1 (SEQ ID NO:18) and Gm.miR395_2 (SEQ ID NO:19)) and miR4392 (Gm.miR4392_1 (SEQ ID NO:21) and Gm.miR4392_2 (SEQ ID NO:22)) were operably linked using a DNA spacer (SP-ART.8a-1, SEQ ID NO:24) to construct SUP-miR395 (SEQ ID NO:20) and SUP-miR4392 (SEQ ID NO:23), respectively. SUP-miR395 and SUP-miR4392 were in turn operably linked to the TIC7941PL_1 coding sequence 3' after the stop codon producing the transgenes, TIC7941PL_1-miR395 (SEQ ID NO:25) and

TIC7941PL_1-miR4392 (SEQ ID NO:26), respectively. Expression of TIC7941PL_1-miR395 and TIC7941PL_1-miR4392 had no effect on the pesticidal activity of TIC7941PL_1. Both TIC7941PL_1-miR395 and TIC7941PL_1-miR4392 demonstrated similar pesticidal activity against Southern armyworm (SAW, *Spodoptera eridania*), Soybean looper (SBL, *Chrysodeixis includens*), and Soybean podworm (SPW, *Helicoverpa zea*) when compared to TIC7941PL_1 in leaf disc assay. Operably linking the miR395 and miR4392 target sites to the TIC7941PL_1 coding sequence is intended to lower expression of the TIC7941PL_1 pesticidal protein in the reproductive tissues of transgenic soybean expressing TIC7941PL_1-miR395 or TIC7941PL_1-miR4392.

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

EXAMPLES

Example 1

Discovery, Cloning, and Expression of TIC7941

A sequence encoding a novel *Paenibacillus lentimorbus* pesticidal protein was identified, cloned, sequence confirmed, and tested in insect bioassay. The pesticidal protein, TIC7941 isolated from the *Paenibacillus lentimorbus* species DSC020651, represents a novel Vip3C-like protein. Distant-related sequences to TIC7941 are Vip3Ca1 (at 72.43% identity, the closest known relative), Vip3Aa1 (64.45% identity), and a Vip3B-like protein (59% identity).

A full length copy of the coding region for TIC7941 and a His-tagged version of TIC7941 (TIC7941_His) were synthesized by methods known in the art and comprise the translational initiation and termination codons of each coding sequence. The TIC7941 coding sequence was cloned using methods known in the art into a Bt expression vector in operable linkage with a Bt expressible promoter. The Bt expression vector comprised a promoter that is on during the sporulation stage of the bacillus. In addition, the TIC7941_His coding sequence was cloned into a vector used for protein expression in *Escherichia coli* (*E. coli*). For isolation of the *E. coli* expressed proteins, a Histidine tag was operably linked to the expressed coding sequences to facilitate column purification of the protein. The coding sequences and their respective protein sequences used for bacterial expression are presented in Table 2.

TABLE 2

| Toxin coding sequences and corresponding protein sequences used for expression in Bt and *E. coli*. | | | |
|---|---|---|---|
| Toxin | DNA Coding Sequence SEQ ID NO: | Protein SEQ ID NO: | Bacterial Expression Host |
| TIC7941 | 1 | 2 | Bt |
| TIC7941_His | 5 | 6 | *E. coli* |

Example 2

TIC7941 Demonstrates Lepidopteran Activity in Insect Bioassay

The pesticidal protein TIC7941 was expressed in Bt and *E. coli* and assayed for toxicity to various species of Lepidoptera, Coleoptera, Hemiptera, and Dipteran. Preparations of TIC7941 and TIC7941_His from both Bt and *E. coli,* were assayed against the Lepidopteran species Black cutworm (BCW, *Agrotis ipsilon*), Corn earworm (CEW, also known as Soybean podworm (SPW), *Helicoverpa zea*), European corn borer (ECB, *Ostrinia nubilalis*), Fall armyworm (FAW, *Spodoptera frugiperda*), Southern armyworm (SAW, *Spodoptera eridania*), Soybean looper (SBL, *Chrysodeixis includens*), Southwestern corn borer (SWCB, *Diatraea grandiosella*), Tobacco budworm (TBW, *Heliothis virescens*), and Velvet bean caterpillar (VBW, *Anticarsia gemmatalis*); the Coleopteran species Colorado potato beetle (CPB, *Leptinotarsa decemlineata*), and Western Corn Rootworm (WCB, *Diabrotica virgifera virgifera*); and the Hemipteran species Tarnished plant bug (TPB, *Lygus lineolaris*) and Western tarnished plant bug (WTP, *Lygus hesperus*); and the Dipteran species Yellow Fever Mosquito (YFM, *Aedes aegypti*).

To produce TIC7941 in Bt hosts, a Bt strain expressing TIC7941 was grown for twenty four (24) hours and then the culture was added to insect diet. Mortality and stunting were evaluated by comparing the growth and development of insects on a diet with a culture from the Bt strain expressing TIC7941 to insects on a diet with an untreated control culture.

The *E. coli* strain expressing TIC7941_His was treated in a similar manner to the Bt strain and was provided in an insect diet after protein purification and compared to the growth and development of insects on a diet with an untreated control culture. TIC7941 demonstrated pesticidal activity against the Lepidopteran insect pest species Black cutworm, Corn earworm, European corn borer, Southern armyworm, Soybean looper and Southwestern corn borer. Activity was particularly high against Soybean looper.

Example 3

Assay of TIC7941PL_1 Activity Against Lepidopteran Pests in Stably Transformed Corn Plants A binary plant transformation vector comprising a transgene cassette designed to express untargeted TIC7941PL_1 pesticidal protein was cloned using methods known in the art. The resulting vector was used to stably transform corn plants. Tissues were harvested from the transformants and used in insect bioassay against various Lepidopteran insect pests.

A synthetic coding sequence was constructed for use in expression of the TIC7941 in plants, cloned into a binary plant transformation vector, and used to transform corn plant cells. The synthetic sequence was synthesized, according to methods generally described in U.S. Pat. No. 5,500,365, to avoid certain inimical problem sequences such as ATTTA and A/T rich plant polyadenylation sequences while preserving the amino acid sequence of the native *Paenibacillus* protein. The synthetic coding sequence (SEQ ID NO:3) encodes a TIC7941PL_1 protein (SEQ ID NO:4) which comprises an additional alanine residue immediately following the initiating methionine relative to the TIC7941 protein. The resulting plant transformation vector comprised a first transgene cassette for expression of the TIC7941PL_1 pesticidal protein which comprised a constitutive promoter, operably linked 5' to a leader, operably linked 5' to an intron, operably linked 5' to the synthetic coding sequence encoding an untargeted TIC7941PL_1 protein (SEQ ID NO:4), which was in turn operably linked 5' to a 3' UTR; and a second transgene cassette for the selection of transformed plant cells using glyphosate selection.

Corn plant cells were transformed with the binary transformation vector as described above using an *Agrobacterium*-mediated transformation method. The transformed cells were induced to form plants by methods known in the art. Bioassays using plant leaf disks were performed analogous to those described in U.S. Pat. No. 8,344,207. A single freshly hatched neonate larvae less than one day old was placed on each leaf disc sample and allowed to feed for approximately four days. A non-transformed corn plant was used to obtain tissue to be used as a negative control. Multiple transformation $R_0$ single-copy insertion events from each binary vector were assessed against BCW, CEW, FAW, and SWCB.

Twelve transformed $R_0$ events were evaluated using plant leaf discs. A leaf damage ratings (LDR) of one, three, or four was given for each event for each insect pest species assayed. An LDR of one (1) is equivalent to less than or equal to thirty percent damage. An LDR of three (3) is equivalent to thirty percent to less than or equal to fifty percent damage. An LDR of four (4) is equivalent to greater than fifty percent damage. The LDR scores for each event and each insect pest species is presented in Table 3.

TABLE 3

Leaf damage ratings (LDR) for transformed corn $R_0$ events expressing TIC7941PL_1.

| Event | $R_0$ Leaf Damage Ratings | | | |
|---|---|---|---|---|
| | BCW | CEW | FAW | SWCB |
| Event 1 | 1 | 1 | 4 | 3 |
| Event 2 | 1 | 1 | 4 | 1 |
| Event 3 | 4 | 4 | 4 | 4 |
| Event 4 | 4 | 4 | 4 | 4 |
| Event 5 | 1 | 1 | 4 | 3 |
| Event 6 | 1 | 1 | 4 | 1 |
| Event 7 | 4 | 4 | 4 | 4 |
| Event 8 | 4 | 4 | 4 | 4 |
| Event 9 | 1 | 1 | 4 | 4 |
| Event 10 | 4 | 4 | 4 | 4 |
| Event 11 | 1 | 1 | 4 | 3 |
| Event 12 | 1 | 1 | 4 | 1 |

As can be seen in Table 3, seven out of the twelve transformed $R_0$ events assayed demonstrated resistance to BCW and CEW. Three of the seven events also demonstrated resistance to SWCB.

Events one through six were selected for assay at the $F_1$ generation. Table 4 shows the LDR scores for each of the six events assayed against the four insect pest species.

TABLE 4

Leaf damage ratings (LDR) for transformed corn $F_1$ events expressing TIC7941PL_1.

| | $F_1$ Leaf Damage Ratings | | | |
|---|---|---|---|---|
| Event | BCW | CEW | FAW | SWCB |
| Event 1 | 1 | 1 | 4 | 1 |
| Event 2 | 1 | 3 | 4 | 1 |
| Event 3 | 1 | 1 | 4 | 3 |
| Event 4 | 1 | 1 | 4 | 3 |
| Event 5 | 1 | 1 | 4 | 3 |
| Event 6 | 1 | 1 | 4 | 3 |

As can be seen in Table 4, all six events demonstrated resistance against BCW, five of the six events demonstrated resistance against CEW, and two of the six events demonstrated resistance against SWCB. Corn plants stably transformed with a transgene cassette for the expression of TIC7941 demonstrates resistance to Lepidopteran pest species such as BCW, CEW, and SWCB.

Example 4

Assay of TIC7941PL_1 Activity Against Lepidopteran Pests in Stably Transformed Soybean Plants Binary plant transformation vectors comprising transgene cassettes designed to express untargeted TIC7941PL_1 pesticidal protein were cloned using methods known in the art. The resulting vectors were used to stably transform soybean plants. Tissues were harvested from the transformants and used in insect bioassay against various Lepidopteran insect pests.

The synthetic TIC7941PL_1 coding sequence designed for plant expression as described in Example 3 was cloned into binary plant transformation vectors, and used to transform soybean plant cells. The binary vectors comprising an untargeted TIC7941PL_1 coding sequence were constructed using methods known in the art. The resulting plant transformation vectors comprised a first transgene cassette for expression of the TIC7941PL_1 pesticidal protein which comprised a plant expressible promoter, operably linked 5' to a leader, operably linked 5' to a synthetic coding sequence encoding an untargeted TIC7941PL_1 protein (SEQ ID NO:4), which was in turn operably linked 5' to a 3' UTR and; a second transgene cassette for the selection of transformed plant cells using spectinomycin selection. Four (4) binary transformation vectors were constructed as described above. Each construct comprised a TIC7941PL_1 expression cassette comprising different promoters and 3' UTRs.

The transformed soybean cells were induced to form plants by methods known in the art. Bioassays using plant leaf disks were performed analogous to those described in U.S. Pat. No. 8,344,207. A non-transformed soybean plant was used to obtain tissue to be used as a negative control. Multiple transformation events from each binary vector were assessed against SAW, SBL, SPW, and VBW.

$R_0$ events, derived from transformations using the four different binary constructs, were evaluated using plant leaf discs. A leaf damage rating (LDR) of one through four was given for each event for each insect pest species assayed. An LDR of one (1) is equivalent to less than or equal to twenty percent damage. An LDR of two (2) is equivalent to twenty percent to less than or equal to thirty five percent damage. An LDR of three (3) is equivalent to thirty five percent to less than or equal to seventy percent damage. An LDR of four (4) is equivalent to greater than seventy percent damage. The LDR scores for each construct and each insect pest species is presented in Table 5. The number of events demonstrating the LDR score (observed) relative to the number of events assayed is also provided. High penetrance of the resistance trait is defined as an LDR score of one (1) wherein greater than fifty percent (50%) of the events demonstrate an LDR of one (1).

TABLE 5

Leaf damage ratings (LDR) and penetrance for transformed soybean $R_0$ events expressing TIC7941PL_1.

| | LDR (Observed/Assayed) | | | |
|---|---|---|---|---|
| Construct | SAW | SBL | SPW | VBC |
| Construct 1 | 1 (12/14) | 1 (13/14) | 1 (12/14) | 2 (1/13) |
| Construct 2 | 1 (14/14) | 1 (14/14) | 1 (13/14) | 3 (9/14) |
| Construct 3 | 1 (12/12) | 1 (12/12) | 1 (12/12) | 3 (5/12) |
| Construct 4 | 1 (12/15) | 1 (15/15) | 1 (12/15) | 3 (10/15) |

As can be seen in Table 5, $R_0$ soybean events expressing TIC7941PL_1 transformed with each of the four (4) constructs demonstrated high resistance with high penetrance to SAW, SBL, and SPW. Stably transformed soybean plants expressing TIC7941PL_1 demonstrate resistance to Lepidopteran pest species, and is highly efficacious against SAW, SBL, and SPW.

Example 5

Assay of TIC7941PL_1 Activity Against Lepidopteran Pests in Stably Transformed Cotton Plants Binary plant transformation vectors comprising transgene cassettes designed to express both plastid targeted and untargeted TIC7941PL_1 pesticidal protein are cloned using methods known in the art. The resulting vectors are used to stably transform cotton plants. Tissues are harvested from the transformants and used in insect bioassay against various Lepidopteran insect pests.

The synthetic coding sequence designed for plant expression as described in Example 3 is cloned into binary plant transformation vectors, and used to transform cotton plant cells. Binary vectors comprising plastid targeted and untargeted TIC7941PL_1 coding sequences are constructed using methods known in the art. The resulting plant transformation vectors comprise a first transgene cassette for expression of the TIC7941PL_1 pesticidal protein which comprises a constitutive promoter, operably linked 5' to a leader, operably linked 5' to a synthetic coding sequence encoding a plastid targeted or untargeted TIC7941PL_1 protein, which is in turn operably linked 5' to a 3' UTR and; a second transgene cassette for the selection of transformed plant cells using spectinomycin selection.

The transformed cotton cells are induced to form plants by methods known in the art. Bioassays using plant leaf disks are performed analogous to those described in U.S. Pat. No. 8,344,207. A non-transformed cotton plant is used to obtain tissue to be used as a negative control. Multiple transformation events from each binary vector are assessed against CBW, FAW, SBL, and TBW, as well as any other Lepidopteran insect pest species known to cause agronomic damage to cotton crops.

In addition to leaf discs, other tissues can also be used to assess resistance imparted by expression of TIC7941PL_1 toxin protein in transgenic cotton plants, such as squares and bolls. Damage rating scores are applied to each sample corresponding to each insect pest and compared to negative controls to determine if expression of TIC7941PL_1 provides resistance to a particular insect pest species.

Example 6

Improving the Pesticidal Activity of TIC7941 Against Fall Armyworm

This example illustrates the improvement of the pesticidal activity of TIC7941 against Fall armyworm through insertion of a FAW transmembrane ABC transporter (ABCc4) binding peptide into the TIC7941 protein sequence.

The peptide fragment FAWPEPBIN (presented as SEQ ID NO:17) binds to the FAW transmembrane ABC transporter ABCc4. FAWPEPBIN_Bac (SEQ ID NO:15) is a synthetic coding sequence encoding FAWPEPBIN (SEQ ID NO:17) for expression of the FAWPEPBIN peptide in bacteria.

Engineered His-tagged TIC7941 proteins with the FAWPEPBIN peptide inserted into different positions in the domain 2 loop of the protein were compared in insect bioassay. The TIC7941_2His coding sequence (SEQ ID NO:7) encodes the TIC7941_2His pesticidal protein (SEQ ID NO:8). The TIC7941_3His coding sequence (SEQ ID NO:9) encodes the TIC7941_3His pesticidal protein (SEQ ID NO:10). The FAWPEPBIN_Bac synthetic coding sequence is found within nucleotide positions 2413-2448 of TIC7941_2His and within positions 2410-2445 of TIC7941_3His. The FAWPEPBIN peptide sequence is located at amino acid positions 805 to 816 of TIC7941_2His and amino acid positions 804 to 815 of TIC7941_3His.

The pesticidal activity of the TIC7941_His, TIC7941_2His, and TIC7941_3His pesticidal proteins were assayed against FAW. Both TIC7941_His and TIC7941_2His demonstrated little or no activity against FAW. However, TIC7941_3His demonstrated improved pesticidal activity against FAW. Thus, insertion of the synthetic coding sequence FAWPEPBIN_Bac in the amino acid positions 804-815 of TIC7941_3His improved the pesticidal activity of the TIC7941 protein against FAW.

Example 7

Assay of Activity of TIC7941PL_2 and TIC7941PL_3 Against Fall Armyworm in Stably Transformed Corn Plants Binary plant transformation vectors comprising transgene cassettes designed to express the TIC7941PL_2 and TIC7941PL_3 pesticidal proteins are cloned using methods known in the art. The resulting vectors are used to stably transform corn plants. Tissues are harvested from the transformants and used in insect bioassay against FAW and other Lepidopteran insect pests.

Binary plant transformation vectors are constructed as previously described in Example 3. The binary vectors comprise a transgene cassette used to express TIC7941PL_2 or TIC7941PL_3. TIC7941PL_2 and TIC7941PL_3 comprise the ABCc4 receptor binding peptide FAWPEPBIN. A synthetic DNA sequence (FAWPEPBIN_PL, SEQ ID NO:16) used for expression in a plant cell and encoding the Fall armyworm transmembrane ABC transporter ABCc4 binding peptide FAWPEPBIN, is inserted into the TIC7941PL_1 toxin protein. The FAWPEPBIN_PL encoding DNA fragment is found within nucleotide positions 2386-2421 of TIC7941PL_2 and within 2383-2418 of TIC7941PL_3. The FAWPEPBIN peptide fragment is located at amino acid positions 796-807 of TIC7941PL_2 and 795-806 of TIC7941PL_3.

Corn plant cells are transformed with the binary transformation vectors as described above using an Agrobacterium-mediated transformation method. The transformed cells are induced to form plants by methods known in the art. Bioassays using plant leaf disks are performed analogous to those described in U.S. Pat. No. 8,344,207. A non-transformed corn plant was used to obtain tissue to be used as a negative control. Multiple transformation $R_0$ single-copy insertion events from each binary vector are assessed against FAW and compared to TIC7941PL_1 to determine if insertion of the FAWPEPBIN peptide increases the insecticidal activity of TIC7941PL_1 against FAW.

Example 8

Reduction of TIC7941PL_1 Expression in the Reproductive Tissue of Stably Transformed Soybean Plants Through the Use of miRNA Target Sites This example illustrates the reduction of expression of TIC7941PL_1 in the reproductive tissues of stably transformed soybean plants through the use of operably linked miRNA recognition sites.

Plant miRNAs regulate target genes at the post-transcriptional level via two major mechanisms: transcript cleavage and translation repression. In addition, some miRNAs also trigger the production of secondary short interfering RNAs (siRNAs) from their transcripts, amplifying the effect of the miRNA on expression. miRNAs are usually twenty-one (21) nucleotides in length, but those that trigger the production of secondary siRNAs, are twenty-two (22) nucleotides in length. Through data mining of miRNAs in various tissues in soybean, two miRNAs were identified that were over-represented in reproductive tissues when compared to vegetative tissues; miR395 and miR4392. miR395 is processed into a twenty one (21) nucleotide miRNA/miRNA* duplex and is expressed mostly in the soybean flower stamen. miR4392 is processed into a twenty two (22) nucleotide miRNA/miRNA* duplex and triggers the production of secondary siRNAs from its transcripts, amplifying the suppression signal. miR4392 is highly enriched in the soybean flower anthers. Bound with an ARGO protein to form a silencing complex, miRNAs function as sequence-specific guides, directing the silencing complex to transcripts through base pairing between the miRNA and the miRNA target binding sites within the 3' untranslated region (3' UTR) of the target RNAs.

Target sites corresponding to miR395 (Gm.miR395_1 (SEQ ID NO:18) and Gm.miR395_2 (SEQ ID NO:19)) were operably linked using the DNA spacer (SP-ART.8a-1, SEQ ID NO:24) to construct SUP-miR395 (SEQ ID NO:20). Target sites corresponding to miR4392 (Gm.miR4392_1 (SEQ ID NO:21) and Gm.miR4392_2 (SEQ ID NO:22)) were operably linked using the DNA spacer (SP-ART.8a-1, SEQ ID NO:24) to construct SUP-miR4392 (SEQ ID NO:23). SUP-miR395 and SUP-miR4392 were operably linked to the TIC7941PL_1 coding sequence 3' after the stop codon producing the transgenes, TIC7941PL_1-miR395 (SEQ ID NO:25) and TIC7941PL_1-miR4392 (SEQ ID NO:26), respectively.

Binary plant transformation vectors comprising transgene cassettes designed to express untargeted TIC7941PL_1-miR395 and TIC7941PL_1-miR4392 were constructed using methods known in the art and were similar to those described in Example 4. Two constructs were constructed using the same promoter, leader and 3' UTR elements as Construct 3 in Example 4 and comprised the TIC7941PL_1-miR395 and TIC7941PL_1-miR4392 DNA sequences. Multiple transformation events from each binary vector were assessed using leaf discs against SAW, SBL, SPW, and VBW as described in in Example 4. Construct 3, TIC7941PL_1, served as a control for comparison of insecticidal activity of the constructs comprising untargeted TIC7941PL_1-miR395 and TIC7941PL_1-miR4392

TABLE 6

Leaf damage ratings (LDR) and penetrance for transformed soybean R₀ events expressing TIC7941PL_1.

| Construct | TIC7941 Composition | LDR (Observed/Assayed) | | | |
|---|---|---|---|---|---|
| | | SAW | SBL | SPW | VBC |
| Construct 3 | TIC7941PL_1 | 1 (12/12) | 1 (12/12) | 1 (12/12) | 3 (5/12) |
| Construct 5 | TIC7941PL_1-mi395 | 1 (20/20) | 1 (20/20) | 1 (20/20) | 3 (9/20) |
| Construct 6 | TIC7941PL_1-mi4392 | 1 (17/19) | 1 (17/19) | 1 (16/19) | 3 (3/19) |

As can be seen in Table 6, operably linking miRNA target binding sites to the TIC7941PL_1 coding sequence did not affect the insecticidal activity of TIC7941PL_1. The two miRNA target binding site constructs demonstrated the same level of insecticidal activity against SAW, SBL, SPW, and VBC. As previously observed in Example 4, TIC7941PL_1 demonstrated high resistance with high penetrance against SAW, SBL, and SPW.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

SEQUENCE LISTING

```
<160> NUMBER OF SEQ ID NOS: 26

<210> SEQ ID NO 1
<211> LENGTH: 2424
<212> TYPE: DNA
<213> ORGANISM: Paenibacillus lentimorbus
<220> FEATURE:
<221> NAME/KEY: misc_feature
<222> LOCATION: (1)..(2424)
<223> OTHER INFORMATION: A nucleic acid sequence encoding a TIC7941
      pesticidal protein obtained from Paenibacillus lentimorbus species
      DSC020651.

<400> SEQUENCE: 1
atgaagcaga ataataattt aagtgtaaga gccttaccaa gttttattga tgtttttaat      60
ggaatttatg gttttgccac tggtattcaa gatatttta acatgatttt tggaacagat     120
acaggtggtc taacactaga agaagtttta aaaaatcaag atttacttta tgagatttct     180
ggtaaacttg atgggattaa tggagaccta agtgagatta ttgcgcaggg aaatttgaat     240
acagaattaa ctaaggaatt gctaaaaatc gctaatgagc agaacaattt attaactgat     300
gttaataaca aactcaatgc gataaatgcg atgctcaaca catatcttcc taaaattaca     360
aatatgttaa gcgatattat gaaacaaaat tatgtcctga gtcttcaaat agaatatctc     420
agtaaacaac tacaggagat ttcagataaa cttgatgtta ttaatttaaa tgtactcatc     480
aactctacac tcacagaaat cactcctgca tatcaacgta ttaaatatgt aaatgaaaaa     540
tttgatgatt taactcttgc tacagaaaaa actctaagag caaaacaagg tagttctaac     600
gaagatattt ttgataatga tactcttgaa aatttaactg agctaactga actagcgaaa     660
```

```
agtgtaacaa aaaatgatgt ggatagtttc gagttttatc tccatacatt ccatgatgta    720
ttgattggca ataatttatt tggtcgttcg gctttaaaaa cagctgcaga attgattact    780
aaagacgaga taaagacgag tggaagtgag ataggaaaag tttatagttt cttaattgta    840
ctaacttgtc tacaagcaaa agcctatctc actttaacgg catgccgaaa attattgggc    900
ttatcagata ttgattatac gaatattcta aatcagcatc taaatgatga aaagaatgaa    960
tttcgtgata acatacttcc tacactgtcc aataaatttt ctaaccctaa ttatgcaaaa   1020
actacaggaa gtgatgatga tgcagtagtt gttttagagg ctgatctagg atatgcctta   1080
attggatttg aaattattag tgatccaatc ccggtattaa aagtatatca agctaagcta   1140
aaacaaaatt atcaagttga cgagcagtcg ttaacagaga aggtgtatcg gaatatcaat   1200
aaaatatttt gtccagaaaa ttccgatcaa cgttattata ttaaagatat aacgtttcct   1260
attggatatg ttattactaa aattatcttt gaaaagaagt accaaaaccg tctgggatat   1320
ctggtaaaag caaatttcta tgattcgtct acaggagata ttgatttgaa taagtcaata   1380
gaggaatcat caggaaattt acttgcttgg cctccggatt ctattataag tattagtaag   1440
gatgaagagg atgaaaagga tgtttatatg ccattaggtg ttatcagcga aacatttttg   1500
accccaatcc atagttttgg attaaaagtt gatgaagaat caagaataat aaccttaaca   1560
ggtaaatctt atctacgaga atatttatta gaatctgatt taaaaaataa agagacaagc   1620
ctgattgctc cgcctaatgt ttttatcagt aatatcgtag aaaattggaa catagaagcg   1680
gatagtctag aaccatgggt tgcaaataac aagaatgcgt atgtcgatag tacaggcggt   1740
atagagggat ctaaagctct atttactcaa ggtgatgggg aattttcaca atttattgga   1800
gataaattaa aacctaacac agattatatg attcaatata ctgtaaaagg aaaaccggcc   1860
atttatttga aacacaaaga tgctactgga tatattatgt acgaagatac aaacggtaat   1920
tatgaagatt ttcaaactag agctgtaaaa tttacttcag gagccgagcc ttcacaagca   1980
catttgattt ttaaaagtca aagtggatat gaggcttggg gggacaactt tattattcta   2040
gaaagtaagt cagttgaatt tgatcaaaag cttgaggctc cagaagtgat aaaatctgaa   2100
aattggattt taactggaga tgctaaatta gaacaagatg ggcaggcgct cagaagtgtg   2160
tcaggaaatg gtagttttaa gcaatttctt caattaaaaa gtgactcaat ttattttatg   2220
aatttccatg ttgttggaaa agcgagggtg acgataaaaa attcacacag agtattattt   2280
gaaaaggatt attcaaccca gtatcgtatc gtggatgatg aatattttac taccgtatct   2340
gatatagatg ggtcttcat agaacttact tcacattctg aggaaagttc agaatttggt    2400
ttttggggct tctctataaa gtaa                                           2424
```

```

<210> SEQ ID NO 2
<211> LENGTH: 807
<212> TYPE: PRT
<213> ORGANISM: Paenibacillus lentimorbus
<220> FEATURE:
<221> NAME/KEY: MISC_FEATURE
<222> LOCATION: (1)..(807)
<223> OTHER INFORMATION: The amino acid sequence of the TIC7941
      pesticidal protein.

<400> SEQUENCE: 2

Met Lys Gln Asn Asn Asn Leu Ser Val Arg Ala Leu Pro Ser Phe Ile
1               5                   10                  15

Asp Val Phe Asn Gly Ile Tyr Gly Phe Ala Thr Gly Ile Gln Asp Ile
            20                  25                  30
```

```
Phe Asn Met Ile Phe Gly Thr Asp Thr Gly Gly Leu Thr Leu Glu Glu
             35                  40                  45
Val Leu Lys Asn Gln Asp Leu Leu Tyr Glu Ile Ser Gly Lys Leu Asp
 50                  55                  60
Gly Ile Asn Gly Asp Leu Ser Glu Ile Ile Ala Gln Gly Asn Leu Asn
 65                  70                  75                  80
Thr Glu Leu Thr Lys Glu Leu Leu Lys Ile Ala Asn Glu Gln Asn Asn
                 85                  90                  95
Leu Leu Thr Asp Val Asn Asn Lys Leu Asn Ala Ile Asn Ala Met Leu
                100                 105                 110
Asn Thr Tyr Leu Pro Lys Ile Thr Asn Met Leu Ser Asp Ile Met Lys
                115                 120                 125
Gln Asn Tyr Val Leu Ser Leu Gln Ile Glu Tyr Leu Ser Lys Gln Leu
            130                 135                 140
Gln Glu Ile Ser Asp Lys Leu Asp Val Ile Asn Leu Asn Val Leu Ile
145                 150                 155                 160
Asn Ser Thr Leu Thr Glu Ile Thr Pro Ala Tyr Gln Arg Ile Lys Tyr
                    165                 170                 175
Val Asn Glu Lys Phe Asp Asp Leu Thr Leu Ala Thr Glu Lys Thr Leu
                180                 185                 190
Arg Ala Lys Gln Gly Ser Ser Asn Glu Asp Ile Phe Asp Asn Asp Thr
            195                 200                 205
Leu Glu Asn Leu Thr Glu Leu Thr Glu Leu Ala Lys Ser Val Thr Lys
            210                 215                 220
Asn Asp Val Asp Ser Phe Glu Phe Tyr Leu His Thr Phe His Asp Val
225                 230                 235                 240
Leu Ile Gly Asn Asn Leu Phe Gly Arg Ser Ala Leu Lys Thr Ala Ala
                245                 250                 255
Glu Leu Ile Thr Lys Asp Glu Ile Lys Thr Ser Gly Ser Glu Ile Gly
                260                 265                 270
Lys Val Tyr Ser Phe Leu Ile Val Leu Thr Cys Leu Gln Ala Lys Ala
            275                 280                 285
Tyr Leu Thr Leu Thr Ala Cys Arg Lys Leu Leu Gly Leu Ser Asp Ile
            290                 295                 300
Asp Tyr Thr Asn Ile Leu Asn Gln His Leu Asn Asp Glu Lys Asn Glu
305                 310                 315                 320
Phe Arg Asp Asn Ile Leu Pro Thr Leu Ser Asn Lys Phe Ser Asn Pro
                325                 330                 335
Asn Tyr Ala Lys Thr Thr Gly Ser Asp Asp Ala Val Val Val Leu
                340                 345                 350
Glu Ala Asp Leu Gly Tyr Ala Leu Ile Gly Phe Glu Ile Ile Ser Asp
            355                 360                 365
Pro Ile Pro Val Leu Lys Val Tyr Gln Ala Lys Leu Lys Gln Asn Tyr
370                 375                 380
Gln Val Asp Glu Gln Ser Leu Thr Glu Lys Val Tyr Arg Asn Ile Asn
385                 390                 395                 400
Lys Ile Phe Cys Pro Glu Asn Ser Asp Gln Arg Tyr Tyr Ile Lys Asp
                405                 410                 415
Ile Thr Phe Pro Ile Gly Tyr Val Ile Thr Lys Ile Ile Phe Glu Lys
                420                 425                 430
Lys Tyr Gln Asn Arg Leu Gly Tyr Leu Val Lys Ala Asn Phe Tyr Asp
            435                 440                 445
Ser Ser Thr Gly Asp Ile Asp Leu Asn Lys Ser Ile Glu Glu Ser Ser
```

```
                450                 455                 460
Gly Asn Leu Leu Ala Trp Pro Pro Asp Ser Ile Ile Ser Ile Ser Lys
465                 470                 475                 480

Asp Glu Glu Asp Glu Lys Asp Val Tyr Met Pro Leu Gly Val Ile Ser
                485                 490                 495

Glu Thr Phe Leu Thr Pro Ile His Ser Phe Gly Leu Lys Val Asp Glu
                500                 505                 510

Glu Ser Arg Ile Ile Thr Leu Thr Gly Lys Ser Tyr Leu Arg Glu Tyr
                515                 520                 525

Leu Leu Glu Ser Asp Leu Lys Asn Lys Glu Thr Ser Leu Ile Ala Pro
                530                 535                 540

Pro Asn Val Phe Ile Ser Asn Ile Val Glu Asn Trp Asn Ile Glu Ala
545                 550                 555                 560

Asp Ser Leu Glu Pro Trp Val Ala Asn Asn Lys Asn Ala Tyr Val Asp
                565                 570                 575

Ser Thr Gly Gly Ile Glu Gly Ser Lys Ala Leu Phe Thr Gln Gly Asp
                580                 585                 590

Gly Glu Phe Ser Gln Phe Ile Gly Asp Lys Leu Lys Pro Asn Thr Asp
                595                 600                 605

Tyr Met Ile Gln Tyr Thr Val Lys Gly Lys Pro Ala Ile Tyr Leu Lys
                610                 615                 620

His Lys Asp Ala Thr Gly Tyr Ile Met Tyr Glu Asp Thr Asn Gly Asn
625                 630                 635                 640

Tyr Glu Asp Phe Gln Thr Arg Ala Val Lys Phe Thr Ser Gly Ala Glu
                645                 650                 655

Pro Ser Gln Ala His Leu Ile Phe Lys Ser Gln Ser Gly Tyr Glu Ala
                660                 665                 670

Trp Gly Asp Asn Phe Ile Ile Leu Glu Ser Lys Ser Val Glu Phe Asp
                675                 680                 685

Gln Lys Leu Glu Ala Pro Glu Val Ile Lys Ser Glu Asn Trp Ile Leu
                690                 695                 700

Thr Gly Asp Ala Lys Leu Glu Gln Asp Gly Gln Ala Leu Arg Ser Val
705                 710                 715                 720

Ser Gly Asn Gly Ser Phe Lys Gln Phe Leu Gln Leu Lys Ser Asp Ser
                725                 730                 735

Ile Tyr Phe Met Asn Phe His Val Val Gly Lys Ala Arg Val Thr Ile
                740                 745                 750

Lys Asn Ser His Arg Val Leu Phe Glu Lys Asp Tyr Ser Thr Gln Tyr
                755                 760                 765

Arg Ile Val Asp Asp Glu Tyr Phe Thr Thr Val Ser Asp Ile Asp Gly
                770                 775                 780

Val Phe Ile Glu Leu Thr Ser His Ser Glu Glu Ser Ser Glu Phe Gly
785                 790                 795                 800

Phe Trp Gly Phe Ser Ile Lys
                805

<210> SEQ ID NO 3
<211> LENGTH: 2427
<212> TYPE: DNA
<213> ORGANISM: Artificial
<220> FEATURE:
<223> OTHER INFORMATION: A synthetic coding sequence encoding a
      TIC7941PL_1 pesticidal protein designed for expression in a plant
      cell wherein an additional alanine codon is inserted immediately
      following

<400> SEQUENCE: 3

```
atggctaagc agaacaacaa cctctccgtg cgcgcgctgc cgagcttcat cgacgtcttc      60
aacggcatct acgggttcgc cacgggcatc caggacatct tcaacatgat ctttgggact     120
gatacgggcg gcctgaccct ggaggaggtg ttaaagaacc aggatctcct ctacgagatt     180
tcgggcaagc tggacgggat caacggcgac ctgagcgaga tcatcgccca gggcaacctc     240
aacaccgagc tcacgaaaga actactgaag attgccaacg agcagaacaa cctgctcacg     300
gacgtgaaca acaagctgaa cgccatcaac gcgatgctga cacctacct gcccaagatc      360
accaacatgc tgagcgacat catgaagcag aactacgtcc tgtcccttca gatcgagtac     420
ctgtccaagc agctccagga gatctcggac aagttggacg tgatcaacct caacgtgctc     480
atcaactcga ccctcaccga gatcactcca gcgtaccagc gcatcaagta cgtcaacgag     540
aagttcgacg acctgacgct ggccactgag aagaccctgc gcgcgaagca aggctcgtcc     600
aacgaggaca tcttcgacaa cgacaccctg gagaacctca cggagctgac cgagctggcc     660
aagagcgtga cgaagaacga cgtggactcg ttcgagttct acctccacac tttccacgac     720
gtcctgatcg ggaacaacct ctttggtcgt tcggccctca agacggcggc ggagctcatc     780
acaaaggacg agatcaagac ctctgggtct gagatcggca aggtgtactc gtttctcatt     840
gtcctgacgt gcctgcaagc gaaggcttac ctaacgctca cggcgtgccg caagctgctg     900
ggcctgtctg acatcgacta caccaacatc ctgaaccagc ccttaacga cgagaagaac      960
gagttccggg acaacattct tcctaccctg tcgaacaagt tcagcaaccc gaactacgcg    1020
aagaccacgg gcagcgacga cgatgcgtg gtggtcctgg aggctgacct gggctacgcg     1080
ctgatcggct tcgagatcat cagcgaccct atcccagtgc tcaaggtgta ccaggcgaag    1140
ctgaaacaga actaccaggt tgacgagcag tccctgacgg agaaggtgta ccggaacatc    1200
aataagatct tctgcccgga gaactccgac cagcggtact acatcaagga catcaccttc    1260
cctatcgggt acgtcatcac caagataatc ttcgagaaga gtaccagaa ccgactcggc     1320
tacctggtga aggcgaactt ctatgacagc tcgacgggcg catcgacct caacaagtcc     1380
atcgaggaga gtagcgggaa tctgctggcg tggccgcccg acagcatcat ctccatctcc    1440
aaggacgagg aagacgagaa ggatgtgtac atgccactag gcgtcatctc cgaaactttc    1500
ctgacaccca tacacagctt cgggctcaag gtggacgagg agagccggat catcacgctg    1560
accggcaaga gctacctccg agagtacctg ctggagtcgg acctcaagaa caaggagacg    1620
tcgctgatcg ctcctcccaa cgtcttcatc tccaacatcg tcgagaactg gaacatcgag    1680
gcggacagcc tggagccgtg ggtggcgaac aacaagaacg cttacgtgga ctcaaccggc    1740
ggcattgagg gctccaaggc cctattcacg caaggcgacg gcgagttcag ccagttcatc    1800
ggcgacaagc taaagcccaa cacggactac atgatccagt acactgtgaa gggcaagccc    1860
gcgatctacc tcaagcacaa ggacgcaacc ggctacatca tgtacgagga caccaacggc    1920
aactacgagg acttccagac gcgggccgtc aagttcacct cgggcgctga gccgtcccag    1980
gcccacttga tcttcaagtc ccagtcgggc tacgaggctt ggggcgacaa ctttatcatc    2040
ctggagagca gtcggtgga gttcgaccag aaactcgagg ctccggaggt catcaagtcg     2100
gagaactgga tactgactgg cgacgcgaag ctggaacagg acggccaggc cctgaggtcc    2160
gtgagcggga acggcagctt caagcagttc ctccagctca gtccgacag catctacttt     2220
atgaacttcc acgtcgtggg caaggcgcgc gtgactatca gaacagcca ccgcgtcctc     2280
ttcgagaagg actacagcac gcagtatcgc atagtcgatg atgaatactt caccaccgtc    2340
```

```
tccgacatcg acggcgtgtt catcgagctg acgtcgcact ccgaggagtc ctccgagttc   2400
ggcttctggg gcttcagcat caagtag                                      2427
```

<210> SEQ ID NO 4
<211> LENGTH: 808
<212> TYPE: PRT
<213> ORGANISM: Artificial
<220> FEATURE:
<223> OTHER INFORMATION: The amino acid sequence of TIC7941PL_1 and
      wherein an additional alanine amino acid is inserted immediately
      following the initiating methionine.

<400> SEQUENCE: 4

```
Met Ala Lys Gln Asn Asn Leu Ser Val Arg Ala Leu Pro Ser Phe
 1               5                  10                  15

Ile Asp Val Phe Asn Gly Ile Tyr Gly Phe Ala Thr Gly Ile Gln Asp
                20                  25                  30

Ile Phe Asn Met Ile Phe Gly Thr Asp Thr Gly Gly Leu Thr Leu Glu
            35                  40                  45

Glu Val Leu Lys Asn Gln Asp Leu Leu Tyr Glu Ile Ser Gly Lys Leu
        50                  55                  60

Asp Gly Ile Asn Gly Asp Leu Ser Glu Ile Ile Ala Gln Gly Asn Leu
65                  70                  75                  80

Asn Thr Glu Leu Thr Lys Glu Leu Leu Lys Ile Ala Asn Glu Gln Asn
                85                  90                  95

Asn Leu Leu Thr Asp Val Asn Asn Lys Leu Asn Ala Ile Asn Ala Met
            100                 105                 110

Leu Asn Thr Tyr Leu Pro Lys Ile Thr Asn Met Leu Ser Asp Ile Met
        115                 120                 125

Lys Gln Asn Tyr Val Leu Ser Leu Gln Ile Glu Tyr Leu Ser Lys Gln
    130                 135                 140

Leu Gln Glu Ile Ser Asp Lys Leu Asp Val Ile Asn Leu Asn Val Leu
145                 150                 155                 160

Ile Asn Ser Thr Leu Thr Glu Ile Thr Pro Ala Tyr Gln Arg Ile Lys
                165                 170                 175

Tyr Val Asn Glu Lys Phe Asp Asp Leu Thr Leu Ala Thr Glu Lys Thr
            180                 185                 190

Leu Arg Ala Lys Gln Gly Ser Ser Asn Glu Asp Ile Phe Asp Asn Asp
        195                 200                 205

Thr Leu Glu Asn Leu Thr Glu Leu Thr Glu Leu Ala Lys Ser Val Thr
    210                 215                 220

Lys Asn Asp Val Asp Ser Phe Glu Phe Tyr Leu His Thr Phe His Asp
225                 230                 235                 240

Val Leu Ile Gly Asn Asn Leu Phe Gly Arg Ser Ala Leu Lys Thr Ala
                245                 250                 255

Ala Glu Leu Ile Thr Lys Asp Glu Ile Lys Thr Ser Gly Ser Glu Ile
            260                 265                 270

Gly Lys Val Tyr Ser Phe Leu Ile Val Leu Thr Cys Leu Gln Ala Lys
        275                 280                 285

Ala Tyr Leu Thr Leu Thr Ala Cys Arg Lys Leu Leu Gly Leu Ser Asp
    290                 295                 300

Ile Asp Tyr Thr Asn Ile Leu Asn Gln His Leu Asn Asp Glu Lys Asn
305                 310                 315                 320

Glu Phe Arg Asp Asn Ile Leu Pro Thr Leu Ser Asn Lys Phe Ser Asn
                325                 330                 335
```

-continued

```
Pro Asn Tyr Ala Lys Thr Thr Gly Ser Asp Asp Ala Val Val
        340                 345             350

Leu Glu Ala Asp Leu Gly Tyr Ala Leu Ile Gly Phe Glu Ile Ile Ser
            355                 360                 365

Asp Pro Ile Pro Val Leu Lys Val Tyr Gln Ala Lys Leu Lys Gln Asn
        370                 375                 380

Tyr Gln Val Asp Glu Gln Ser Leu Thr Glu Lys Val Tyr Arg Asn Ile
385                 390                 395                 400

Asn Lys Ile Phe Cys Pro Glu Asn Ser Asp Gln Arg Tyr Tyr Ile Lys
                405                 410                 415

Asp Ile Thr Phe Pro Ile Gly Tyr Val Ile Thr Lys Ile Ile Phe Glu
            420                 425                 430

Lys Lys Tyr Gln Asn Arg Leu Gly Tyr Leu Val Lys Ala Asn Phe Tyr
        435                 440                 445

Asp Ser Ser Thr Gly Asp Ile Asp Leu Asn Lys Ser Ile Glu Glu Ser
        450                 455                 460

Ser Gly Asn Leu Leu Ala Trp Pro Pro Asp Ser Ile Ile Ser Ile Ser
465                 470                 475                 480

Lys Asp Glu Glu Asp Glu Lys Asp Val Tyr Met Pro Leu Gly Val Ile
                485                 490                 495

Ser Glu Thr Phe Leu Thr Pro Ile His Ser Phe Gly Leu Lys Val Asp
            500                 505                 510

Glu Glu Ser Arg Ile Ile Thr Leu Thr Gly Lys Ser Tyr Leu Arg Glu
        515                 520                 525

Tyr Leu Leu Glu Ser Asp Leu Lys Asn Lys Glu Thr Ser Leu Ile Ala
        530                 535                 540

Pro Pro Asn Val Phe Ile Ser Asn Ile Val Glu Asn Trp Asn Ile Glu
545                 550                 555                 560

Ala Asp Ser Leu Glu Pro Trp Val Ala Asn Asn Lys Asn Ala Tyr Val
                565                 570                 575

Asp Ser Thr Gly Gly Ile Glu Gly Ser Lys Ala Leu Phe Thr Gln Gly
            580                 585                 590

Asp Gly Glu Phe Ser Gln Phe Ile Gly Asp Lys Leu Lys Pro Asn Thr
        595                 600                 605

Asp Tyr Met Ile Gln Tyr Thr Val Lys Gly Lys Pro Ala Ile Tyr Leu
        610                 615                 620

Lys His Lys Asp Ala Thr Gly Tyr Ile Met Tyr Glu Asp Thr Asn Gly
625                 630                 635                 640

Asn Tyr Glu Asp Phe Gln Thr Arg Ala Val Lys Phe Thr Ser Gly Ala
                645                 650                 655

Glu Pro Ser Gln Ala His Leu Ile Phe Lys Ser Gln Ser Gly Tyr Glu
            660                 665                 670

Ala Trp Gly Asp Asn Phe Ile Ile Leu Glu Ser Lys Ser Val Glu Phe
        675                 680                 685

Asp Gln Lys Leu Glu Ala Pro Glu Val Ile Lys Ser Glu Asn Trp Ile
        690                 695                 700

Leu Thr Gly Asp Ala Lys Leu Glu Gln Asp Gly Gln Ala Leu Arg Ser
705                 710                 715                 720

Val Ser Gly Asn Gly Ser Phe Lys Gln Phe Leu Gln Leu Lys Ser Asp
                725                 730                 735

Ser Ile Tyr Phe Met Asn Phe His Val Val Gly Lys Ala Arg Val Thr
            740                 745                 750
```

```
Ile Lys Asn Ser His Arg Val Leu Phe Glu Lys Asp Tyr Ser Thr Gln
            755                 760                 765

Tyr Arg Ile Val Asp Asp Glu Tyr Phe Thr Thr Val Ser Asp Ile Asp
        770                 775                 780

Gly Val Phe Ile Glu Leu Thr Ser His Ser Glu Glu Ser Ser Glu Phe
785                 790                 795                 800

Gly Phe Trp Gly Phe Ser Ile Lys
                805

<210> SEQ ID NO 5
<211> LENGTH: 2481
<212> TYPE: DNA
<213> ORGANISM: Artificial
<220> FEATURE:
<223> OTHER INFORMATION: A nucleic acid sequence encoding a TIC7941_His
      pesticidal protein, wherein a nucleic acid sequence encoding a
      Histidine tag is operably linked 5' and in frame to the TIC7941
      coding sequence.

<400> SEQUENCE: 5
atgcatcacc atcaccatca ccatcaccat cacggtaccg agaccgtccg cttccaatcc      60
aagcagaata taatttaag tgtaagagcc ttaccaagtt ttattgatgt ttttaatgga     120
atttatggtt ttgccactgg tattcaagat attttttaaca tgattttttgg aacagataca   180 ggtggtctaa cactagaaga agttttaaaa aatcaagatt tacttttatga gatttctggt     240 aaacttgatg ggattaatgg agacctaagt gagattattg cgcagggaaa tttgaataca     300
gaattaacta aggaattgct aaaaatcgct aatgagcaga acaatttatt aactgatgtt     360
aataacaaac tcaatgcgat aaatgcgatg ctcaacacat atcttcctaa aattacaaat     420
atgttaagcg atattatgaa acaaaattat gtcctgagtc ttcaaataga atatctcagt     480
aaacaactac aggagatttc agataaactt gatgttatta atttaaatgt actcatcaac     540
tctacactca cagaaaatca ctcctgcatat caacgtatta aatatgtaaa tgaaaaattt     600
gatgatttaa ctcttgctac agaaaaaact ctaagagcaa acaaggtag ttctaacgaa      660 gatattttttg ataatgatac tcttgaaaat ttaactgagc taactgaact agcgaaaagt     720
gtaacaaaaa atgatgtgga tagtttcgag ttttatctcc atacattcca tgatgtattg     780
attggcaata attttatttgg tcgttcggct ttaaaaacag ctgcagaatt gattactaaa    840
gacgagataa agacgagtgg aagtgagata ggaaaagttt tagtttctt aattgtacta     900 acttgtctac aagcaaaagc ctatctcact ttaacggcat gccgaaaatt attgggctta    960
tcagatattg attatacgaa tattctaaat cagcatctaa atgatgaaaa gatgaatttt    1020
cgtgataaca tacttcctac actgtccaat aaattttcta accctaatta tgcaaaaact    1080
acaggaagtg atgatgatgc agtagttgtt ttagaggctg atctaggata tgccttaatt    1140
ggatttgaaa ttattagtga tccaatcccg gtattaaaag tatatcaagc taagctaaaa    1200
caaaattatc aagttgacga gcagtcgtta acagagaagg tgtatcggaa tatcaataaa    1260
atattttgtc cagaaaattc cgatcaacgt tattatatta aagatataac gtttcctatt    1320
ggatatgtta ttactaaaat tatcttttgaa aagaagtacc aaaaccgtct gggatatctg    1380
gtaaaagcaa atttctatga ttcgtctaca ggagatattg atttgaataa gtcaatagag    1440
gaatcatcag gaaatttact tgcttggcct ccggattcta ttataagtat tagtaaggat    1500
gaagaggatg aaaaggatgt ttatatgcca ttaggtgtta tcagcgaaac attttttgacc   1560 ccaatccata gttttttggatt aaaagttgat gaagaatcaa gaataataac cttaacaggt    1620
```

-continued

```
aaatcttatc tacgagaata tttattagaa tctgatttaa aaaataaaga gacaagcctg    1680
attgctccgc ctaatgtttt tatcagtaat atcgtagaaa attggaacat agaagcggat    1740
agtctagaac catgggttgc aaataacaag aatgcgtatg tcgatagtac aggcggtata    1800
gagggatcta aagctctatt tactcaaggt gatggggaat tttcacaatt tattggagat    1860
aaattaaaac ctaacacaga ttatatgatt caatatactg taaaaggaaa accggccatt    1920
tatttgaaac acaagatgc tactggatat attatgtacg aagatacaaa cggtaattat    1980
gaagattttc aaactagagc tgtaaaattt acttcaggag ccgagccttc acaagcacat    2040
ttgattttta aaagtcaaag tggatatgag gcttgggggg acaactttat tattctagaa    2100
agtaagtcag ttgaatttga tcaaaagctt gaggctccag aagtgataaa atctgaaaat    2160
tggattttaa ctggagatgc taaattagaa caagatgggc aggcgctcag aagtgtgtca    2220
ggaaatggta gttttaagca atttcttcaa ttaaaaagtg actcaattta ttttatgaat    2280
ttccatgttg ttggaaaagc gagggtgacg ataaaaaatt cacacagagt attatttgaa    2340
aaggattatt caacccagta tcgtatcgtg gatgatgaat attttactac cgtatctgat    2400
atagatgggg tcttcataga acttacttca cattctgagg aaagttcaga atttggtttt    2460
tggggcttct ctataaagta a                                              2481
```

<210> SEQ ID NO 6
<211> LENGTH: 826
<212> TYPE: PRT
<213> ORGANISM: Artificial
<220> FEATURE:
<223> OTHER INFORMATION: The amino acid sequence of the TIC7941_His pesticidal protein.

<400> SEQUENCE: 6

```
Met His His His His His His His His His Gly Thr Glu Thr Val
1               5                   10                  15

Arg Phe Gln Ser Lys Gln Asn Asn Leu Ser Val Arg Ala Leu Pro
            20                  25                  30

Ser Phe Ile Asp Val Phe Asn Gly Ile Tyr Gly Phe Ala Thr Gly Ile
        35                  40                  45

Gln Asp Ile Phe Asn Met Ile Phe Gly Thr Asp Thr Gly Gly Leu Thr
    50                  55                  60

Leu Glu Glu Val Leu Lys Asn Gln Asp Leu Leu Tyr Glu Ile Ser Gly
65                  70                  75                  80

Lys Leu Asp Gly Ile Asn Gly Asp Leu Ser Glu Ile Ile Ala Gln Gly
                85                  90                  95

Asn Leu Asn Thr Glu Leu Thr Lys Glu Leu Leu Lys Ile Ala Asn Glu
            100                 105                 110

Gln Asn Asn Leu Leu Thr Asp Val Asn Asn Lys Leu Asn Ala Ile Asn
        115                 120                 125

Ala Met Leu Asn Thr Tyr Leu Pro Lys Ile Thr Asn Met Leu Ser Asp
    130                 135                 140

Ile Met Lys Gln Asn Tyr Val Leu Ser Leu Gln Ile Glu Tyr Leu Ser
145                 150                 155                 160

Lys Gln Leu Gln Glu Ile Ser Asp Lys Leu Asp Val Ile Asn Leu Asn
                165                 170                 175

Val Leu Ile Asn Ser Thr Leu Thr Glu Ile Thr Pro Ala Tyr Gln Arg
            180                 185                 190

Ile Lys Tyr Val Asn Glu Lys Phe Asp Asp Leu Thr Leu Ala Thr Glu
        195                 200                 205
```

```
Lys Thr Leu Arg Ala Lys Gln Gly Ser Ser Asn Glu Asp Ile Phe Asp
    210                 215                 220
Asn Asp Thr Leu Glu Asn Leu Thr Glu Leu Thr Glu Leu Ala Lys Ser
225                 230                 235                 240
Val Thr Lys Asn Asp Val Asp Ser Phe Glu Phe Tyr Leu His Thr Phe
                245                 250                 255
His Asp Val Leu Ile Gly Asn Asn Leu Phe Gly Arg Ser Ala Leu Lys
            260                 265                 270
Thr Ala Ala Glu Leu Ile Thr Lys Asp Glu Ile Lys Thr Ser Gly Ser
        275                 280                 285
Glu Ile Gly Lys Val Tyr Ser Phe Leu Ile Val Leu Thr Cys Leu Gln
290                 295                 300
Ala Lys Ala Tyr Leu Thr Leu Thr Ala Cys Arg Lys Leu Leu Gly Leu
305                 310                 315                 320
Ser Asp Ile Asp Tyr Thr Asn Ile Leu Asn Gln His Leu Asn Asp Glu
                325                 330                 335
Lys Asn Glu Phe Arg Asp Asn Ile Leu Pro Thr Leu Ser Asn Lys Phe
            340                 345                 350
Ser Asn Pro Asn Tyr Ala Lys Thr Thr Gly Ser Asp Asp Ala Val
        355                 360                 365
Val Val Leu Glu Ala Asp Leu Gly Tyr Ala Leu Ile Gly Phe Glu Ile
370                 375                 380
Ile Ser Asp Pro Ile Pro Val Leu Lys Val Tyr Gln Ala Lys Leu Lys
385                 390                 395                 400
Gln Asn Tyr Gln Val Asp Glu Gln Ser Leu Thr Glu Lys Val Tyr Arg
                405                 410                 415
Asn Ile Asn Lys Ile Phe Cys Pro Glu Asn Ser Asp Gln Arg Tyr Tyr
            420                 425                 430
Ile Lys Asp Ile Thr Phe Pro Ile Gly Tyr Val Ile Thr Lys Ile Ile
        435                 440                 445
Phe Glu Lys Lys Tyr Gln Asn Arg Leu Gly Tyr Leu Val Lys Ala Asn
450                 455                 460
Phe Tyr Asp Ser Ser Thr Gly Asp Ile Asp Leu Asn Lys Ser Ile Glu
465                 470                 475                 480
Glu Ser Ser Gly Asn Leu Leu Ala Trp Pro Pro Asp Ser Ile Ile Ser
                485                 490                 495
Ile Ser Lys Asp Glu Glu Asp Glu Lys Asp Val Tyr Met Pro Leu Gly
            500                 505                 510
Val Ile Ser Glu Thr Phe Leu Thr Pro Ile His Ser Phe Gly Leu Lys
        515                 520                 525
Val Asp Glu Glu Ser Arg Ile Ile Thr Leu Thr Gly Lys Ser Tyr Leu
530                 535                 540
Arg Glu Tyr Leu Leu Glu Ser Asp Leu Lys Asn Lys Glu Thr Ser Leu
545                 550                 555                 560
Ile Ala Pro Pro Asn Val Phe Ile Ser Asn Ile Val Glu Asn Trp Asn
                565                 570                 575
Ile Glu Ala Asp Ser Leu Glu Pro Trp Val Ala Asn Asn Lys Asn Ala
            580                 585                 590
Tyr Val Asp Ser Thr Gly Gly Ile Glu Gly Ser Lys Ala Leu Phe Thr
        595                 600                 605
Gln Gly Asp Gly Glu Phe Ser Gln Phe Ile Gly Asp Lys Leu Lys Pro
610                 615                 620
```

```
Asn Thr Asp Tyr Met Ile Gln Tyr Thr Val Lys Gly Lys Pro Ala Ile
625                 630                 635                 640

Tyr Leu Lys His Lys Asp Ala Thr Gly Tyr Ile Met Tyr Glu Asp Thr
            645                 650                 655

Asn Gly Asn Tyr Glu Asp Phe Gln Thr Arg Ala Val Lys Phe Thr Ser
        660                 665                 670

Gly Ala Glu Pro Ser Gln Ala His Leu Ile Phe Lys Ser Gln Ser Gly
    675                 680                 685

Tyr Glu Ala Trp Gly Asp Asn Phe Ile Ile Leu Glu Ser Lys Ser Val
690                 695                 700

Glu Phe Asp Gln Lys Leu Glu Ala Pro Glu Val Ile Lys Ser Glu Asn
705                 710                 715                 720

Trp Ile Leu Thr Gly Asp Ala Lys Leu Glu Gln Asp Gly Gln Ala Leu
            725                 730                 735

Arg Ser Val Ser Gly Asn Gly Ser Phe Lys Gln Phe Leu Gln Leu Lys
        740                 745                 750

Ser Asp Ser Ile Tyr Phe Met Asn Phe His Val Val Gly Lys Ala Arg
    755                 760                 765

Val Thr Ile Lys Asn Ser His Arg Val Leu Phe Glu Lys Asp Tyr Ser
770                 775                 780

Thr Gln Tyr Arg Ile Val Asp Asp Glu Tyr Phe Thr Thr Val Ser Asp
785                 790                 795                 800

Ile Asp Gly Val Phe Ile Glu Leu Thr Ser His Ser Glu Glu Ser Ser
            805                 810                 815

Glu Phe Gly Phe Trp Gly Phe Ser Ile Lys
            820                 825

<210> SEQ ID NO 7
<211> LENGTH: 2481
<212> TYPE: DNA
<213> ORGANISM: Artificial
<220> FEATURE:
<223> OTHER INFORMATION: A nucleic acid sequence encoding a
      TIC7941PL_2His pesticidal protein, wherein a nucleic acid sequence
      encoding a Histidine tag is operably linked 5' and in frame.

<400> SEQUENCE: 7
atgggcagca gccatcatca tcatcatcac cacaagcaga ataataattt aagtgtaaga      60
gccttaccaa gttttattga tgttttaat ggaatttatg ttttgccac tggtattcaa      120 gatatttta acatgatttt tggaacagat acaggtggtc taacactaga agaagtttta      180
aaaaatcaag atttactta tgagatttct ggtaaacttg atgggattaa tggagaccta      240
agtgagatta ttgcgcaggg aaatttgaat acagaattaa ctaaggaatt gctaaaaatc      300
gctaatgagc agaacaattt attaactgat gttaataaca aactcaatgc gataaatgcg      360
atgctcaaca catatcttcc taaaattaca aatatgttaa gcgatattat gaaacaaaat      420
tatgtcctga gtcttcaaat agaatatctc agtaaacaac tacaggagat tcagataaaa      480
cttgatgtta ttaatttaaa tgtactcatc aactctacac tcacagaaat cactcctgca      540
tatcaacgta ttaaatatgt aaatgaaaaa tttgatgatt taactcttgc tacagaaaaa      600
actctaagag caaaacaagg tagttctaac gaagatattt tgataatga tactcttgaa      660 aatttaactg agctaactga actagcgaaa agtgtaacaa aaaatgatgt ggatagtttc      720
gagttttatc tccatacatt ccatgatgta ttgattggca ataatttatt tggtcgttcg      780
gctttaaaaa cagctgcaga attgattact aaagacgaga taaagacgag tggaagtgag      840
```

```
ataggaaaag tttatagttt cttaattgta ctaacttgtc tacaagcaaa agcctatctc    900
actttaacgg catgccgaaa attattgggc ttatcagata ttgattatac gaatattcta    960
aatcagcatc taaatgatga aaagaatgaa tttcgtgata acatacttcc tacactgtcc   1020
aataaatttt ctaaccctaa ttatgcaaaa actacaggaa gtgatgatga tgcagtagtt   1080
gttttagagg ctgatctagg atatgcctta attggatttg aaattattag tgatccaatc   1140
ccggtattaa aagtatatca agctaagcta aacaaaatt atcaagttga cgagcagtcg    1200
ttaacagaga aggtgtatcg gaatatcaat aaaatatttt gtccagaaaa ttccgatcaa   1260
cgttattata ttaaagatat aacgtttcct attggatatg ttattactaa aattatcttt   1320 gaaagaagt accaaaaccg tctgggatat ctggtaaaag caaatttcta tgattcgtct    1380
acaggagata ttgatttgaa taagtcaata gaggaatcat caggaaattt acttgcttgg   1440
cctccggatt ctattataag tattagtaag gatgaagagg atgaaaagga tgtttatatg   1500
ccattaggtg ttatcagcga acattttttg accccaatcc atagttttgg attaaaagtt   1560
gatgaagaat caagaataat aaccttaaca ggtaaatctt atctacgaga atatttatta   1620
gaatctgatt taaaaaataa agagacaagc ctgattgctc cgcctaatgt ttttatcagt   1680
aatatcgtag aaaattggaa catagaagcg gatagtctag aaccatgggt tgcaaataac   1740
aagaatgcgt atgtcgatag tacaggcggt atagagggat ctaaagctct atttactcaa   1800
ggtgatgggg aattttcaca atttattgga gataaattaa aacctaacac agattatatg   1860
attcaatata ctgtaaaagg aaaaccggcc atttatttga aacacaaaga tgctactgga   1920
tatattatgt acgaagatac aaacggtaat tatgaagatt ttcaaactag agctgtaaaa   1980
tttacttcag gagccgagcc ttcacaagca catttgattt ttaaaagtca aagtggatat   2040
gaggcttggg gggacaactt tattattcta gaaagtaagt cagttgaatt tgatcaaaag   2100
cttgaggctc cagaagtgat aaaatctgaa aattggattt taactggaga tgctaaatta   2160
gaacaagatg ggcaggcgct cagaagtgtg tcaggaaatg gtagttttaa gcaatttctt   2220
caattaaaaa gtgactcaat ttatttttatg aatttccatg ttgttggaaa agcgagggtg   2280
acgataaaaa attcacacag agtattattt gaaaaggatt attcaaccca gtatcgtatc   2340
gtggatgatg aatatttttac taccgtatct gatatagatg gggtcttcat agaacttact   2400
tcacattctg agtcttcttt agcagatatt atgtctttat ggggagaaga atttggtttt   2460
tggggcttct ctataaagta g                                             2481
```

<210> SEQ ID NO 8
<211> LENGTH: 826
<212> TYPE: PRT
<213> ORGANISM: Artificial
<220> FEATURE:
<223> OTHER INFORMATION: The amino acid sequence of the TIC7941PL_2His
      pesticidal protein.

<400> SEQUENCE: 8

Met Gly Ser Ser His His His His His His Lys Gln Asn Asn Asn
1               5                   10                  15

Leu Ser Val Arg Ala Leu Pro Ser Phe Ile Asp Val Phe Asn Gly Ile
            20                  25                  30

Tyr Gly Phe Ala Thr Gly Ile Gln Asp Ile Phe Asn Met Ile Phe Gly
        35                  40                  45

Thr Asp Thr Gly Gly Leu Thr Leu Glu Glu Val Leu Lys Asn Gln Asp
    50                  55                  60

-continued

```
Leu Leu Tyr Glu Ile Ser Gly Lys Leu Asp Gly Ile Asn Gly Asp Leu
 65                  70                  75                  80

Ser Glu Ile Ile Ala Gln Gly Asn Leu Asn Thr Glu Leu Thr Lys Glu
                 85                  90                  95

Leu Leu Lys Ile Ala Asn Glu Gln Asn Asn Leu Leu Thr Asp Val Asn
            100                 105                 110

Asn Lys Leu Asn Ala Ile Asn Ala Met Leu Asn Thr Tyr Leu Pro Lys
        115                 120                 125

Ile Thr Asn Met Leu Ser Asp Ile Met Lys Gln Asn Tyr Val Leu Ser
130                 135                 140

Leu Gln Ile Glu Tyr Leu Ser Lys Gln Leu Gln Glu Ile Ser Asp Lys
145                 150                 155                 160

Leu Asp Val Ile Asn Leu Asn Val Leu Ile Asn Ser Thr Leu Thr Glu
                165                 170                 175

Ile Thr Pro Ala Tyr Gln Arg Ile Lys Tyr Val Asn Glu Lys Phe Asp
            180                 185                 190

Asp Leu Thr Leu Ala Thr Glu Lys Thr Leu Arg Ala Lys Gln Gly Ser
        195                 200                 205

Ser Asn Glu Asp Ile Phe Asp Asn Asp Thr Leu Glu Asn Leu Thr Glu
210                 215                 220

Leu Thr Glu Leu Ala Lys Ser Val Thr Lys Asn Asp Val Asp Ser Phe
225                 230                 235                 240

Glu Phe Tyr Leu His Thr Phe His Asp Val Leu Ile Gly Asn Asn Leu
                245                 250                 255

Phe Gly Arg Ser Ala Leu Lys Thr Ala Ala Glu Leu Ile Thr Lys Asp
            260                 265                 270

Glu Ile Lys Thr Ser Gly Ser Glu Ile Gly Lys Val Tyr Ser Phe Leu
        275                 280                 285

Ile Val Leu Thr Cys Leu Gln Ala Lys Ala Tyr Leu Thr Leu Thr Ala
290                 295                 300

Cys Arg Lys Leu Leu Gly Leu Ser Asp Ile Asp Tyr Thr Asn Ile Leu
305                 310                 315                 320

Asn Gln His Leu Asn Asp Glu Lys Asn Glu Phe Arg Asp Asn Ile Leu
                325                 330                 335

Pro Thr Leu Ser Asn Lys Phe Ser Asn Pro Asn Tyr Ala Lys Thr Thr
            340                 345                 350

Gly Ser Asp Asp Ala Val Val Leu Glu Ala Asp Leu Gly Tyr
        355                 360                 365

Ala Leu Ile Gly Phe Glu Ile Ile Ser Asp Pro Ile Pro Val Leu Lys
370                 375                 380

Val Tyr Gln Ala Lys Leu Lys Gln Asn Tyr Gln Val Asp Glu Gln Ser
385                 390                 395                 400

Leu Thr Glu Lys Val Tyr Arg Asn Ile Asn Lys Ile Phe Cys Pro Glu
                405                 410                 415

Asn Ser Asp Gln Arg Tyr Ile Lys Asp Ile Thr Phe Pro Ile Gly
            420                 425                 430

Tyr Val Ile Thr Lys Ile Ile Phe Glu Lys Lys Tyr Gln Asn Arg Leu
        435                 440                 445

Gly Tyr Leu Val Lys Ala Asn Phe Tyr Asp Ser Ser Thr Gly Asp Ile
450                 455                 460

Asp Leu Asn Lys Ser Ile Glu Glu Ser Gly Asn Leu Leu Ala Trp
465                 470                 475                 480

Pro Pro Asp Ser Ile Ile Ser Ile Ser Lys Asp Glu Glu Asp Glu Lys
```

```
                    485                 490                 495
Asp Val Tyr Met Pro Leu Gly Val Ile Ser Glu Thr Phe Leu Thr Pro
                500                 505                 510

Ile His Ser Phe Gly Leu Lys Val Asp Glu Glu Ser Arg Ile Ile Thr
            515                 520                 525

Leu Thr Gly Lys Ser Tyr Leu Arg Glu Tyr Leu Leu Glu Ser Asp Leu
        530                 535                 540

Lys Asn Lys Glu Thr Ser Leu Ile Ala Pro Pro Asn Val Phe Ile Ser
545                 550                 555                 560

Asn Ile Val Glu Asn Trp Asn Ile Glu Ala Asp Ser Leu Glu Pro Trp
                565                 570                 575

Val Ala Asn Asn Lys Asn Ala Tyr Val Asp Ser Thr Gly Gly Ile Glu
            580                 585                 590

Gly Ser Lys Ala Leu Phe Thr Gln Gly Asp Gly Glu Phe Ser Gln Phe
        595                 600                 605

Ile Gly Asp Lys Leu Lys Pro Asn Thr Asp Tyr Met Ile Gln Tyr Thr
    610                 615                 620

Val Lys Gly Lys Pro Ala Ile Tyr Leu Lys His Lys Asp Ala Thr Gly
625                 630                 635                 640

Tyr Ile Met Tyr Glu Asp Thr Asn Gly Asn Tyr Glu Asp Phe Gln Thr
                645                 650                 655

Arg Ala Val Lys Phe Thr Ser Gly Ala Glu Pro Ser Gln Ala His Leu
            660                 665                 670

Ile Phe Lys Ser Gln Ser Gly Tyr Glu Ala Trp Gly Asp Asn Phe Ile
        675                 680                 685

Ile Leu Glu Ser Lys Ser Val Glu Phe Asp Gln Lys Leu Glu Ala Pro
    690                 695                 700

Glu Val Ile Lys Ser Glu Asn Trp Ile Leu Thr Gly Asp Ala Lys Leu
705                 710                 715                 720

Glu Gln Asp Gly Gln Ala Leu Arg Ser Val Ser Gly Asn Gly Ser Phe
                725                 730                 735

Lys Gln Phe Leu Gln Leu Lys Ser Asp Ser Ile Tyr Phe Met Asn Phe
            740                 745                 750

His Val Gly Lys Ala Arg Val Thr Ile Lys Asn Ser His Arg Val
        755                 760                 765

Leu Phe Glu Lys Asp Tyr Ser Thr Gln Tyr Arg Ile Val Asp Asp Glu
    770                 775                 780

Tyr Phe Thr Thr Val Ser Asp Ile Asp Gly Val Phe Ile Glu Leu Thr
785                 790                 795                 800

Ser His Ser Glu Ser Ser Leu Ala Asp Ile Met Ser Leu Trp Gly Glu
                805                 810                 815

Glu Phe Gly Phe Trp Gly Phe Ser Ile Lys
            820                 825
```

<210> SEQ ID NO 9
<211> LENGTH: 2481
<212> TYPE: DNA
<213> ORGANISM: Artificial
<220> FEATURE:
<223> OTHER INFORMATION: A nucleic acid sequence encoding a
    TIC7941PL_3His pesticidal protein, wherein a nucleic acid sequence
    encoding a Histidine tag is operably linked 5' and in frame.

<400> SEQUENCE: 9
atgggcagca gccatcatca tcatcatcac cacaagcaga taataattt aagtgtaaga      60

```
gccttaccaa gttttattga tgtttttaat ggaatttatg gttttgccac tggtattcaa      120
gatattttta acatgatttt tggaacagat acaggtggtc taacactaga agaagtttta      180
aaaaatcaag atttactttta tgagatttct ggtaaacttg atgggattaa tggagaccta     240
agtgagatta ttgcgcaggg aaatttgaat acagaattaa ctaaggaatt gctaaaaatc     300
gctaatgagc agaacaattt attaactgat gttaataaca aactcaatgc gataaatgcg      360
atgctcaaca catatcttcc taaaattaca aatatgttaa gcgatattat gaaacaaaat      420
tatgtcctga gtcttcaaat agaatatctc agtaaacaac tacaggagat ttcagataaa     480
cttgatgtta ttaatttaaa tgtactcatc aactctacac tcacagaaat cactcctgca      540
tatcaacgta ttaaatatgt aaatgaaaaa tttgatgatt taactcttgc tacagaaaaa     600
actctaagag caaacaagg tagttctaac gaagatattt tgataatga tactcttgaa      660 aatttaactg agctaactga actagcgaaa agtgtaacaa aaaatgatgt ggatagtttc     720
gagttttatc tccatacatt ccatgatgta ttgattggca ataatttatt tggtcgttcg      780
gctttaaaaa cagctgcaga attgattact aaagacgaga taaagacgag tggaagtgag     840
ataggaaaag tttatagttt cttaattgta ctaacttgtc tacaagcaaa agcctatctc      900
actttaacgg catgccgaaa attattgggc ttatcagata ttgattatac gaatattcta      960
aatcagcatc taatgatga aaagaatgaa tttcgtgata acatacttcc tacactgtcc     1020
aataaatttt ctaaccctaa ttatgcaaaa actacaggaa gtgatgatga tgcagtagtt     1080
gttttagagg ctgatctagg atatgcctta attggatttg aaattattag tgatccaatc     1140
ccggtattaa aagtatatca agctaagcta aaacaaaatt atcaagttga cgagcagtcg     1200
ttaacagaga aggtgtatcg gaatatcaat aaaatatttt gtccagaaaa ttccgatcaa     1260
cgttattata ttaaagatat aacgtttcct attggatatg ttattactaa aattatcttt     1320
gaaaagaagt accaaaaccg tctgggatat ctggtaaaag caaatttcta tgattcgtct     1380
acaggagata ttgatttgaa taagtcaata gaggaatcat caggaaattt acttgcttgg     1440
cctccggatt ctattataag tattagtaag gatgaagagg atgaaaagga tgtttatatg     1500
ccattaggtg ttatcagcga acatttttg accccaatcc atagttttgg attaaaagtt      1560
gatgaagaat caagaataat aaccttaaca ggtaaatctt atctacgaga atatttatta     1620
gaatctgatt taaaaaataa agagacaagc ctgattgctc cgcctaatgt ttttatcagt     1680
aatatcgtag aaaattggaa catagaagcg gatagtctag aaccatgggt tgcaaataac     1740
aagaatgcgt atgtcgatag tacaggcggt atagagggct ctaaagctct atttactcaa     1800
ggtgatgggg aattttcaca atttattgga gataaattaa aacctaacac agattatatg     1860
attcaatata ctgtaaaagg aaaaccggcc atttatttga acacaaaga tgctactgga     1920 tatattatgt acgaagatac aaacggtaat tatgaagatt tcaaactag agctgtaaaa     1980 tttacttcag gagccgagcc ttcacaagca catttgattt ttaaaagtca agtggatat     2040 gaggcttggg gggacaactt tattattcta gaaagtaagt cagttgaatt tgatcaaaag    2100
cttgaggctc cagaagtgat aaaatctgaa aattggattt taactggaga tgctaaatta    2160
gaacaagatg gcaggcgct cagaagtgtg tcaggaaatg gtagttttaa gcaattttctt    2220 caattaaaaa gtgactcaat ttattttatg aatttccatg ttgttggaaa agcgagggtg    2280
acgataaaaa attcacacag agtattattt gaaaaggatt attcaaccca gtatcgtatc    2340
gtggatgatg aatattttac taccgtatct gatatagatg gggtcttcat agaacttact    2400
tcacattctt cttctttagc agatattatg tctttatggg gagaatcaga atttggtttt    2460
```
tggggcttct ctataaagta g                                              2481

<210> SEQ ID NO 10
<211> LENGTH: 826
<212> TYPE: PRT
<213> ORGANISM: Artificial
<220> FEATURE:
<223> OTHER INFORMATION: The amino acid sequence of the TIC7941PL_3His
      pesticidal protein.

<400> SEQUENCE: 10

Met Gly Ser Ser His His His His His His Lys Gln Asn Asn Asn
1               5                   10                  15

Leu Ser Val Arg Ala Leu Pro Ser Phe Ile Asp Val Phe Asn Gly Ile
            20                  25                  30

Tyr Gly Phe Ala Thr Gly Ile Gln Asp Ile Phe Asn Met Ile Phe Gly
            35                  40                  45

Thr Asp Thr Gly Gly Leu Thr Leu Glu Glu Val Leu Lys Asn Gln Asp
50                  55                  60

Leu Leu Tyr Glu Ile Ser Gly Lys Leu Asp Gly Ile Asn Gly Asp Leu
65                  70                  75                  80

Ser Glu Ile Ile Ala Gln Gly Asn Leu Asn Thr Glu Leu Thr Lys Glu
                85                  90                  95

Leu Leu Lys Ile Ala Asn Glu Gln Asn Asn Leu Leu Thr Asp Val Asn
            100                 105                 110

Asn Lys Leu Asn Ala Ile Asn Ala Met Leu Asn Thr Tyr Leu Pro Lys
            115                 120                 125

Ile Thr Asn Met Leu Ser Asp Ile Met Lys Gln Asn Tyr Val Leu Ser
130                 135                 140

Leu Gln Ile Glu Tyr Leu Ser Lys Gln Leu Gln Glu Ile Ser Asp Lys
145                 150                 155                 160

Leu Asp Val Ile Asn Leu Asn Val Leu Ile Asn Ser Thr Leu Thr Glu
                165                 170                 175

Ile Thr Pro Ala Tyr Gln Arg Ile Lys Tyr Val Asn Glu Lys Phe Asp
            180                 185                 190

Asp Leu Thr Leu Ala Thr Glu Lys Thr Leu Arg Ala Lys Gln Gly Ser
            195                 200                 205

Ser Asn Glu Asp Ile Phe Asp Asn Asp Thr Leu Glu Asn Leu Thr Glu
210                 215                 220

Leu Thr Glu Leu Ala Lys Ser Val Thr Lys Asn Asp Val Asp Ser Phe
225                 230                 235                 240

Glu Phe Tyr Leu His Thr Phe His Asp Val Leu Ile Gly Asn Asn Leu
                245                 250                 255

Phe Gly Arg Ser Ala Leu Lys Thr Ala Ala Glu Leu Ile Thr Lys Asp
            260                 265                 270

Glu Ile Lys Thr Ser Gly Ser Glu Ile Gly Lys Val Tyr Ser Phe Leu
            275                 280                 285

Ile Val Leu Thr Cys Leu Gln Ala Lys Ala Tyr Leu Thr Leu Thr Ala
290                 295                 300

Cys Arg Lys Leu Leu Gly Leu Ser Asp Ile Asp Tyr Thr Asn Ile Leu
305                 310                 315                 320

Asn Gln His Leu Asn Asp Glu Lys Asn Glu Phe Arg Asp Asn Ile Leu
                325                 330                 335

Pro Thr Leu Ser Asn Lys Phe Ser Asn Pro Asn Tyr Ala Lys Thr Thr
            340                 345                 350

```
Gly Ser Asp Asp Ala Val Val Leu Glu Ala Asp Leu Gly Tyr
        355                 360                 365

Ala Leu Ile Gly Phe Glu Ile Ile Ser Asp Pro Ile Pro Val Leu Lys
370                 375                 380

Val Tyr Gln Ala Lys Leu Lys Gln Asn Tyr Gln Val Asp Glu Gln Ser
385                 390                 395                 400

Leu Thr Glu Lys Val Tyr Arg Asn Ile Asn Lys Ile Phe Cys Pro Glu
                405                 410                 415

Asn Ser Asp Gln Arg Tyr Tyr Ile Lys Asp Ile Thr Phe Pro Ile Gly
                420                 425                 430

Tyr Val Ile Thr Lys Ile Ile Phe Glu Lys Lys Tyr Gln Asn Arg Leu
                435                 440                 445

Gly Tyr Leu Val Lys Ala Asn Phe Tyr Asp Ser Ser Thr Gly Asp Ile
                450                 455                 460

Asp Leu Asn Lys Ser Ile Glu Glu Ser Ser Gly Asn Leu Leu Ala Trp
465                 470                 475                 480

Pro Pro Asp Ser Ile Ile Ser Ile Ser Lys Asp Glu Glu Asp Glu Lys
                485                 490                 495

Asp Val Tyr Met Pro Leu Gly Val Ile Ser Glu Thr Phe Leu Thr Pro
                500                 505                 510

Ile His Ser Phe Gly Leu Lys Val Asp Glu Glu Ser Arg Ile Ile Thr
                515                 520                 525

Leu Thr Gly Lys Ser Tyr Leu Arg Glu Tyr Leu Leu Glu Ser Asp Leu
                530                 535                 540

Lys Asn Lys Glu Thr Ser Leu Ile Ala Pro Pro Asn Val Phe Ile Ser
545                 550                 555                 560

Asn Ile Val Glu Asn Trp Asn Ile Glu Ala Asp Ser Leu Glu Pro Trp
                565                 570                 575

Val Ala Asn Asn Lys Asn Ala Tyr Val Asp Ser Thr Gly Gly Ile Glu
                580                 585                 590

Gly Ser Lys Ala Leu Phe Thr Gln Gly Asp Gly Glu Phe Ser Gln Phe
                595                 600                 605

Ile Gly Asp Lys Leu Lys Pro Asn Thr Asp Tyr Met Ile Gln Tyr Thr
                610                 615                 620

Val Lys Gly Lys Pro Ala Ile Tyr Leu Lys His Lys Asp Ala Thr Gly
625                 630                 635                 640

Tyr Ile Met Tyr Glu Asp Thr Asn Gly Asn Tyr Glu Asp Phe Gln Thr
                645                 650                 655

Arg Ala Val Lys Phe Thr Ser Gly Ala Glu Pro Ser Gln Ala His Leu
                660                 665                 670

Ile Phe Lys Ser Gln Ser Gly Tyr Glu Ala Trp Gly Asp Asn Phe Ile
                675                 680                 685

Ile Leu Glu Ser Lys Ser Val Glu Phe Asp Gln Lys Leu Glu Ala Pro
                690                 695                 700

Glu Val Ile Lys Ser Glu Asn Trp Ile Leu Thr Gly Asp Ala Lys Leu
705                 710                 715                 720

Glu Gln Asp Gly Gln Ala Leu Arg Ser Val Ser Gly Asn Gly Ser Phe
                725                 730                 735

Lys Gln Phe Leu Gln Leu Lys Ser Asp Ser Ile Tyr Phe Met Asn Phe
                740                 745                 750

His Val Val Gly Lys Ala Arg Val Thr Ile Lys Asn Ser His Arg Val
                755                 760                 765
```

```
Leu Phe Glu Lys Asp Tyr Ser Thr Gln Tyr Arg Ile Val Asp Asp Glu
    770                 775                 780

Tyr Phe Thr Thr Val Ser Asp Ile Asp Gly Val Phe Ile Glu Leu Thr
785                 790                 795                 800

Ser His Ser Ser Leu Ala Asp Ile Met Ser Leu Trp Gly Glu Ser
                805                 810                 815

Glu Phe Gly Phe Trp Gly Phe Ser Ile Lys
        820                 825

<210> SEQ ID NO 11
<211> LENGTH: 2454
<212> TYPE: DNA
<213> ORGANISM: Artificial
<220> FEATURE:
<223> OTHER INFORMATION: A synthetic coding sequence encoding a
      TIC7941PL_2 pesticidal protein designed for expression in a plant
      cell wherein an additional alanine codon is inserted immediately
      following the initiating methionine codon.

<400> SEQUENCE: 11
atggctaagc agaacaacaa cctctccgtg cgcgcgctgc cgagcttcat cgacgtcttc      60
aacggcatct acgggttcgc cacgggcatc caggacatct tcaacatgat ctttgggact     120
gatacgggcg gcctgaccct ggaggaggtg ttaaagaacc aggatctcct ctacgagatt     180
tcgggcaagt ggacgggat  caacggcgac ctgagcgaga tcatcgccca ggcaacctc      240 aacaccgagc tcacgaaaga actactgaag attgccaacg agcagaacaa cctgctcacg     300
gacgtgaaca acaagctgaa cgccatcaac gcgatgctga cacctacct gcccaagatc      360 accaacatgc tgagcgacat catgaagcag aactacgtcc tgtcccttca gatcgagtac     420
ctgtccaagc agctccagga gatctcggac aagttggacg tgatcaacct caacgtgctc     480
atcaactcga ccctcaccga gatcactcca gcgtaccagc gcatcaagta cgtcaacgag     540
aagttcgacg acctgacgct ggccactgag aagaccctgc gcgcgaagca aggctcgtcc     600
aacgaggaca tcttcgacaa cgacaccctg gagaacctca cggagctgac cgagctggcc     660
aagagcgtga cgaagaacga cgtggactcg ttcgagttct acctccacac tttccacgac     720
gtcctgatcg ggaacaacct ctttggtcgt tcggccctca gacggcggc ggagctcatc      780 acaaaggacg agatcaagac ctctgggtct gagatcggca aggtgtactc gtttctcatt     840
gtcctgacgt gcctgcaagc gaaggcttac ctaacgctca cggcgtgccg caagctgctg     900
ggcctgtctg acatcgacta caccaacatc ctgaaccagc accttaacga cgagaagaac     960
gagttccggg acaacattct tcctaccctg tcgaacaagt tcagcaaccc gaactacgcg    1020
aagaccacgg gcagcgacga cgatgcggtg gtggtcctgg aggctgacct gggctacgcg    1080
ctgatcggct tcgagatcat cagcgaccct atcccagtgc tcaaggtgta ccaggcgaag    1140
ctgaaacaga actaccaggt tgacgagcag tccctgacgg agaaggtgta ccggaacatc    1200
aataagatct tctgcccgga gaactccgac cagcggtact acatcaagga catcaccttc    1260
cctatcgggt acgtcatcac caagataatc ttcgagaaga agtaccagaa ccgactcggc    1320
tacctggtga aggcgaactt ctatgacagc tcgacgggcg acatcgacct caacaagtcc    1380
atcgaggaga gtagcgggaa tctgctggcg tggccgcccg cacagcatca tctccatctcc   1440 aaggacgagg aagacgagaa ggatgtgtac atgccactag gcgtcatctc cgaaactttc    1500
ctgacaccca tacacagctt cgggctcaag gtggacgagg agagccggat catcacgctg    1560
accggcaaga gctacctccg agagtacctg ctggagtcgg acctcaagaa caaggagacg    1620
```

```
tcgctgatcg ctcctcccaa cgtcttcatc tccaacatcg tcgagaactg gaacatcgag    1680
gcggacagcc tggagccgtg ggtggcgaac aacaagaacg cttacgtgga ctcaaccggc    1740
ggcattgagg gctccaaggc cctattcacg caaggcgacg gcgagttcag ccagttcatc    1800
ggcgacaagc taaagcccaa cacggactac atgatccagt acactgtgaa gggcaagccc    1860
gcgatctacc tcaagcacaa ggacgcaacc ggctacatca tgtacgagga caccaacggc    1920
aactacgagg acttccagac gcgggccgtc aagttcacct cgggcgctga ccgtcccag    1980 gcccacttga tcttcaagtc ccagtcgggc tacgaggctt ggggcgacaa ctttatcatc    2040
ctggagagca gtcggtgga gttcgaccag aaactcgagg ctccggaggt catcaagtcg    2100
gagaactgga tactgactgg cgacgcgaag ctggaacagg acggccaggc cctgaggtcc    2160
gtgagcggga acggcagctt caagcagttc ctccagctca gtccgacag catctacttt    2220 atgaacttcc acgtcgtggg caaggcgcgc gtgactatca agaacagcca ccgcgtcctc    2280
ttcgagaagg actacagcac gcagtatcgc atagtcgatg atgaatactt caccaccgtc    2340
tccgacatcg acgcgtgtt catcgagctg acgtcgcact ccgagagctc gctggcggac    2400
attatgtcgc tgtggggcga agagttcggc ttctggggct tcagcatcaa gtag          2454
```

<210> SEQ ID NO 12
<211> LENGTH: 817
<212> TYPE: PRT
<213> ORGANISM: Artificial
<220> FEATURE:
<223> OTHER INFORMATION: The amino acid sequence of TIC7941PL_2 and
      wherein an additional alanine amino acid is inserted immediately
      following the initiating methionine.

<400> SEQUENCE: 12

```
Met Ala Lys Gln Asn Asn Asn Leu Ser Val Arg Ala Leu Pro Ser Phe
1               5                   10                  15

Ile Asp Val Phe Asn Gly Ile Tyr Gly Phe Ala Thr Gly Ile Gln Asp
            20                  25                  30

Ile Phe Asn Met Ile Phe Gly Thr Asp Thr Gly Gly Leu Thr Leu Glu
        35                  40                  45

Glu Val Leu Lys Asn Gln Asp Leu Leu Tyr Glu Ile Ser Gly Lys Leu
    50                  55                  60

Asp Gly Ile Asn Gly Asp Leu Ser Glu Ile Ile Ala Gln Gly Asn Leu
65                  70                  75                  80

Asn Thr Glu Leu Thr Lys Glu Leu Leu Lys Ile Ala Asn Glu Gln Asn
                85                  90                  95

Asn Leu Leu Thr Asp Val Asn Asn Lys Leu Asn Ala Ile Asn Ala Met
            100                 105                 110

Leu Asn Thr Tyr Leu Pro Lys Ile Thr Asn Met Leu Ser Asp Ile Met
        115                 120                 125

Lys Gln Asn Tyr Val Leu Ser Leu Gln Ile Glu Tyr Leu Ser Lys Gln
    130                 135                 140

Leu Gln Glu Ile Ser Asp Lys Leu Asp Val Ile Asn Leu Asn Val Leu
145                 150                 155                 160

Ile Asn Ser Thr Leu Thr Glu Ile Thr Pro Ala Tyr Gln Arg Ile Lys
                165                 170                 175

Tyr Val Asn Glu Lys Phe Asp Asp Leu Thr Leu Ala Thr Glu Lys Thr
            180                 185                 190

Leu Arg Ala Lys Gln Gly Ser Ser Asn Glu Asp Ile Phe Asp Asn Asp
        195                 200                 205
```

-continued

```
Thr Leu Glu Asn Leu Thr Glu Leu Thr Glu Leu Ala Lys Ser Val Thr
    210                 215                 220

Lys Asn Asp Val Asp Ser Phe Glu Phe Tyr Leu His Thr Phe His Asp
225                 230                 235                 240

Val Leu Ile Gly Asn Asn Leu Phe Gly Arg Ser Ala Leu Lys Thr Ala
                245                 250                 255

Ala Glu Leu Ile Thr Lys Asp Glu Ile Lys Thr Ser Gly Ser Glu Ile
            260                 265                 270

Gly Lys Val Tyr Ser Phe Leu Ile Val Leu Thr Cys Leu Gln Ala Lys
        275                 280                 285

Ala Tyr Leu Thr Leu Thr Ala Cys Arg Lys Leu Leu Gly Leu Ser Asp
290                 295                 300

Ile Asp Tyr Thr Asn Ile Leu Asn Gln His Leu Asn Asp Glu Lys Asn
305                 310                 315                 320

Glu Phe Arg Asp Asn Ile Leu Pro Thr Leu Ser Asn Lys Phe Ser Asn
                325                 330                 335

Pro Asn Tyr Ala Lys Thr Thr Gly Ser Asp Asp Ala Val Val Val
            340                 345                 350

Leu Glu Ala Asp Leu Gly Tyr Ala Leu Ile Gly Phe Glu Ile Ile Ser
        355                 360                 365

Asp Pro Ile Pro Val Leu Lys Val Tyr Gln Ala Lys Leu Lys Gln Asn
370                 375                 380

Tyr Gln Val Asp Glu Gln Ser Leu Thr Glu Lys Val Tyr Arg Asn Ile
385                 390                 395                 400

Asn Lys Ile Phe Cys Pro Glu Asn Ser Asp Gln Arg Tyr Tyr Ile Lys
                405                 410                 415

Asp Ile Thr Phe Pro Ile Gly Tyr Val Ile Thr Lys Ile Ile Phe Glu
            420                 425                 430

Lys Lys Tyr Gln Asn Arg Leu Gly Tyr Leu Val Lys Ala Asn Phe Tyr
        435                 440                 445

Asp Ser Ser Thr Gly Asp Ile Asp Leu Asn Lys Ser Ile Glu Glu Ser
450                 455                 460

Ser Gly Asn Leu Leu Ala Trp Pro Pro Asp Ser Ile Ile Ser Ile Ser
465                 470                 475                 480

Lys Asp Glu Glu Asp Glu Lys Asp Val Tyr Met Pro Leu Gly Val Ile
                485                 490                 495

Ser Glu Thr Phe Leu Thr Pro Ile His Ser Phe Gly Leu Lys Val Asp
            500                 505                 510

Glu Glu Ser Arg Ile Ile Thr Leu Thr Gly Lys Ser Tyr Leu Arg Glu
        515                 520                 525

Tyr Leu Leu Glu Ser Asp Leu Lys Asn Lys Glu Thr Ser Leu Ile Ala
530                 535                 540

Pro Pro Asn Val Phe Ile Ser Asn Ile Val Glu Asn Trp Asn Ile Glu
545                 550                 555                 560

Ala Asp Ser Leu Glu Pro Trp Val Ala Asn Lys Asn Ala Tyr Val
                565                 570                 575

Asp Ser Thr Gly Gly Ile Glu Gly Ser Lys Ala Leu Phe Thr Gln Gly
            580                 585                 590

Asp Gly Glu Phe Ser Gln Phe Ile Gly Asp Lys Leu Lys Pro Asn Thr
        595                 600                 605

Asp Tyr Met Ile Gln Tyr Thr Val Lys Gly Lys Pro Ala Ile Tyr Leu
610                 615                 620

Lys His Lys Asp Ala Thr Gly Tyr Ile Met Tyr Glu Asp Thr Asn Gly
```

```
                625                 630                 635                 640
         Asn Tyr Glu Asp Phe Gln Thr Arg Ala Val Lys Phe Thr Ser Gly Ala
                             645                 650                 655
         Glu Pro Ser Gln Ala His Leu Ile Phe Lys Ser Gln Ser Gly Tyr Glu
                             660                 665                 670
         Ala Trp Gly Asp Asn Phe Ile Ile Leu Glu Ser Lys Ser Val Glu Phe
                         675                 680                 685
         Asp Gln Lys Leu Glu Ala Pro Glu Val Ile Lys Ser Glu Asn Trp Ile
                     690                 695                 700
         Leu Thr Gly Asp Ala Lys Leu Glu Gln Asp Gly Gln Ala Leu Arg Ser
         705                 710                 715                 720
         Val Ser Gly Asn Gly Ser Phe Lys Gln Phe Leu Gln Leu Lys Ser Asp
                             725                 730                 735
         Ser Ile Tyr Phe Met Asn Phe His Val Val Gly Lys Ala Arg Val Thr
                         740                 745                 750
         Ile Lys Asn Ser His Arg Val Leu Phe Glu Lys Asp Tyr Ser Thr Gln
                     755                 760                 765
         Tyr Arg Ile Val Asp Asp Glu Tyr Phe Thr Thr Val Ser Asp Ile Asp
                 770                 775                 780
         Gly Val Phe Ile Glu Leu Thr Ser His Ser Glu Ser Ser Leu Ala Asp
         785                 790                 795                 800
         Ile Met Ser Leu Trp Gly Glu Glu Phe Gly Phe Trp Gly Phe Ser Ile
                             805                 810                 815
         Lys

<210> SEQ ID NO 13
<211> LENGTH: 2454
<212> TYPE: DNA
<213> ORGANISM: Artificial
<220> FEATURE:
<223> OTHER INFORMATION: A synthetic coding sequence encoding a
      TIC7941PL_3 pesticidal protein designed for expression in a plant
      cell wherein an additional alanine codon is inserted immediately
      following the initiating methionine codon.

<400> SEQUENCE: 13
atggctaagc agaacaacaa cctctccgtg cgcgcgctgc cgagcttcat cgacgtcttc       60
aacggcatct acgggttcgc cacgggcatc caggacatct tcaacatgat ctttgggact      120
gatacgggcg gcctgaccct ggaggaggtg ttaaagaacc aggatctcct ctacgagatt      180
tcgggcaagc tggacgggat caacggcgac ctgagcgaga tcatcgccca gggcaacctc      240
aacaccgagc tcacgaaaga actactgaag attgccaacg agcagaacaa cctgctcacg      300
gacgtgaaca acaagctgaa cgccatcaac gcgatgctga cacctacct gcccaagatc      360 accaacatgc tgagcgacat catgaagcag aactacgtcc tgtcccttca gatcgagtac      420
ctgtccaagc agctccagga gatctcggac aagttggacg tgatcaacct caacgtgctc      480
atcaactcga ccctcaccga gatcactcca gcgtaccagc gcatcaagta cgtcaacgag      540
aagttcgacg acctgacgct ggccactgag aagaccctgc gcgcgaagca aggctcgtcc      600
aacgaggaca tcttcgacaa cgacaccctg gagaacctca cggagctgac cgagctggcc      660
aagagcgtga cgaagaacga cgtggactcg ttcgagttct acctccacac tttccacgac      720
gtcctgatcg ggaacaacct ctttggtcgt tcggccctca gacggcggc ggagctcatc      780 acaaaggacg agatcaagac ctctgggtct gagatcggca agtgtactc gtttctcatt      840 gtcctgacgt gcctgcaagc gaaggcttac ctaacgctca cggcgtgccg caagctgctg      900
```

```
ggcctgtctg acatcgacta caccaacatc ctgaaccagc accttaacga cgagaagaac    960
gagttccggg acaacattct tcctaccctg tcgaacaagt tcagcaaccc gaactacgcg   1020
aagaccacgg gcagcgacga cgatgcggtg gtggtcctgg aggctgacct gggctacgcg   1080
ctgatcggct tcgagatcat cagcgaccct atcccagtgc tcaaggtgta ccaggcgaag   1140
ctgaaacaga actaccaggt tgacgagcag tccctgacgg agaaggtgta ccggaacatc   1200
aataagatct tctgcccgga gaactccgac cagcggtact acatcaagga catcaccttc   1260
cctatcgggt acgtcatcac caagataatc ttcgagaaga agtaccagaa ccgactcggc   1320
tacctggtga aggcgaactt ctatgacagc tcgacgggcg acatcgacct caacaagtcc   1380
atcgaggaga gtagcgggaa tctgctggcg tggccgcccg acagcatcat ctccatctcc   1440
aaggacgagg aagacgagaa ggatgtgtac atgccactag gcgtcatctc cgaaactttc   1500
ctgacaccca tacacagctt cgggctcaag gtggacgagg agagccggat catcacgctg   1560
accggcaaga gctacctccg agagtacctg ctggagtcgg acctcaagaa caaggagacg   1620
tcgctgatcg ctcctcccaa cgtcttcatc tccaacatcg tcgagaactg gaacatcgag   1680
gcggacagcc tggagccgtg ggtggcgaac aacaagaacg cttacgtgga ctcaaccggc   1740
ggcattgagg gctccaaggc cctattcacg caaggcgacg gcgagttcag ccagttcatc   1800
ggcgacaagc taaagcccaa cacggactac atgatccagt acactgtgaa gggcaagccc   1860
gcgatctacc tcaagcacaa ggacgcaacc ggctacatca tgtacgagga caccaacggc   1920
aactacgagg acttccagac gcgggccgtc aagttcacct cgggcgctga gccgtcccag   1980
gcccacttga tcttcaagtc ccagtcgggc tacgaggctt ggggcgacaa ctttatcatc   2040
ctggagagca gtcggtgga gttcgaccag aaactcgagg ctccggaggt catcaagtcg   2100
gagaactgga tactgactgg cgacgcgaag ctggaacagg acggccaggc cctgaggtcc   2160
gtgagcggga acggcagctt caagcagttc ctccagctca gtccgacag catctacttt   2220 atgaacttcc acgtcgtggg caaggcgcgc gtgactatca agaacagcca ccgcgtcctc   2280
ttcgagaagg actacagcac gcagtatcgc atagtcgatg atgaatactt caccaccgtc   2340
tccgacatcg acggcgtgtt catcgagctg acgtcgcact ccagctcgct ggcggacatt   2400
atgtcgctgt ggggcgaatc cgagttcggc ttctggggct tcagcatcaa gtag          2454
```

<210> SEQ ID NO 14
<211> LENGTH: 817
<212> TYPE: PRT
<213> ORGANISM: Artificial
<220> FEATURE:
<223> OTHER INFORMATION: The amino acid sequence of TIC7941PL_3 and
      wherein an additional alanine amino acid is inserted immediately
      following the initiating methionine.

<400> SEQUENCE: 14

```
Met Ala Lys Gln Asn Asn Asn Leu Ser Val Arg Ala Leu Pro Ser Phe
1               5                   10                  15

Ile Asp Val Phe Asn Gly Ile Tyr Gly Phe Ala Thr Gly Ile Gln Asp
            20                  25                  30

Ile Phe Asn Met Ile Phe Gly Thr Asp Thr Gly Gly Leu Thr Leu Glu
        35                  40                  45

Glu Val Leu Lys Asn Gln Asp Leu Leu Tyr Glu Ile Ser Gly Lys Leu
    50                  55                  60

Asp Gly Ile Asn Gly Asp Leu Ser Glu Ile Ile Ala Gln Gly Asn Leu
65                  70                  75                  80
```

```
Asn Thr Glu Leu Thr Lys Glu Leu Leu Lys Ile Ala Asn Glu Gln Asn
                85              90              95

Asn Leu Leu Thr Asp Val Asn Asn Lys Leu Asn Ala Ile Asn Ala Met
                100             105             110

Leu Asn Thr Tyr Leu Pro Lys Ile Thr Asn Met Leu Ser Asp Ile Met
                115             120             125

Lys Gln Asn Tyr Val Leu Ser Leu Gln Ile Glu Tyr Leu Ser Lys Gln
                130             135             140

Leu Gln Glu Ile Ser Asp Lys Leu Asp Val Ile Asn Leu Asn Val Leu
145             150             155             160

Ile Asn Ser Thr Leu Thr Glu Ile Thr Pro Ala Tyr Gln Arg Ile Lys
                165             170             175

Tyr Val Asn Glu Lys Phe Asp Asp Leu Thr Leu Ala Thr Glu Lys Thr
                180             185             190

Leu Arg Ala Lys Gln Gly Ser Ser Asn Glu Asp Ile Phe Asp Asn Asp
                195             200             205

Thr Leu Glu Asn Leu Thr Glu Leu Thr Glu Leu Ala Lys Ser Val Thr
                210             215             220

Lys Asn Asp Val Asp Ser Phe Glu Phe Tyr Leu His Thr Phe His Asp
225             230             235             240

Val Leu Ile Gly Asn Asn Leu Phe Gly Arg Ser Ala Leu Lys Thr Ala
                245             250             255

Ala Glu Leu Ile Thr Lys Asp Glu Ile Lys Thr Ser Gly Ser Glu Ile
                260             265             270

Gly Lys Val Tyr Ser Phe Leu Ile Val Leu Thr Cys Leu Gln Ala Lys
                275             280             285

Ala Tyr Leu Thr Leu Thr Ala Cys Arg Lys Leu Leu Gly Leu Ser Asp
                290             295             300

Ile Asp Tyr Thr Asn Ile Leu Asn Gln His Leu Asn Asp Glu Lys Asn
305             310             315             320

Glu Phe Arg Asp Asn Ile Leu Pro Thr Leu Ser Asn Lys Phe Ser Asn
                325             330             335

Pro Asn Tyr Ala Lys Thr Thr Gly Ser Asp Asp Asp Ala Val Val Val
                340             345             350

Leu Glu Ala Asp Leu Gly Tyr Ala Leu Ile Gly Phe Glu Ile Ile Ser
                355             360             365

Asp Pro Ile Pro Val Leu Lys Val Tyr Gln Ala Lys Leu Lys Gln Asn
                370             375             380

Tyr Gln Val Asp Glu Gln Ser Leu Thr Glu Lys Val Tyr Arg Asn Ile
385             390             395             400

Asn Lys Ile Phe Cys Pro Glu Asn Ser Asp Gln Arg Tyr Tyr Ile Lys
                405             410             415

Asp Ile Thr Phe Pro Ile Gly Tyr Val Ile Thr Lys Ile Ile Phe Glu
                420             425             430

Lys Lys Tyr Gln Asn Arg Leu Gly Tyr Leu Val Lys Ala Asn Phe Tyr
                435             440             445

Asp Ser Ser Thr Gly Asp Ile Asp Leu Asn Lys Ser Ile Glu Glu Ser
                450             455             460

Ser Gly Asn Leu Leu Ala Trp Pro Asp Ser Ile Ile Ser Ile Ser
465             470             475             480

Lys Asp Glu Glu Asp Glu Lys Asp Val Tyr Met Pro Leu Gly Val Ile
                485             490             495
```

Ser Glu Thr Phe Leu Thr Pro Ile His Ser Phe Gly Leu Lys Val Asp
            500                 505                 510

Glu Glu Ser Arg Ile Ile Thr Leu Thr Gly Lys Ser Tyr Leu Arg Glu
        515                 520                 525

Tyr Leu Leu Glu Ser Asp Leu Lys Asn Lys Glu Thr Ser Leu Ile Ala
        530                 535                 540

Pro Pro Asn Val Phe Ile Ser Asn Ile Val Glu Asn Trp Asn Ile Glu
545                 550                 555                 560

Ala Asp Ser Leu Glu Pro Trp Val Ala Asn Asn Lys Asn Ala Tyr Val
                565                 570                 575

Asp Ser Thr Gly Gly Ile Glu Gly Ser Lys Ala Leu Phe Thr Gln Gly
            580                 585                 590

Asp Gly Glu Phe Ser Gln Phe Ile Gly Asp Lys Leu Lys Pro Asn Thr
        595                 600                 605

Asp Tyr Met Ile Gln Tyr Thr Val Lys Gly Lys Pro Ala Ile Tyr Leu
        610                 615                 620

Lys His Lys Asp Ala Thr Gly Tyr Ile Met Tyr Glu Asp Thr Asn Gly
625                 630                 635                 640

Asn Tyr Glu Asp Phe Gln Thr Arg Ala Val Lys Phe Thr Ser Gly Ala
                645                 650                 655

Glu Pro Ser Gln Ala His Leu Ile Phe Lys Ser Gln Ser Gly Tyr Glu
            660                 665                 670

Ala Trp Gly Asp Asn Phe Ile Ile Leu Glu Ser Lys Ser Val Glu Phe
        675                 680                 685

Asp Gln Lys Leu Glu Ala Pro Glu Val Ile Lys Ser Glu Asn Trp Ile
        690                 695                 700

Leu Thr Gly Asp Ala Lys Leu Glu Gln Asp Gly Gln Ala Leu Arg Ser
705                 710                 715                 720

Val Ser Gly Asn Gly Ser Phe Lys Gln Phe Leu Gln Leu Lys Ser Asp
                725                 730                 735

Ser Ile Tyr Phe Met Asn Phe His Val Val Gly Lys Ala Arg Val Thr
            740                 745                 750

Ile Lys Asn Ser His Arg Val Leu Phe Glu Lys Asp Tyr Ser Thr Gln
        755                 760                 765

Tyr Arg Ile Val Asp Asp Glu Tyr Phe Thr Thr Val Ser Asp Ile Asp
        770                 775                 780

Gly Val Phe Ile Glu Leu Thr Ser His Ser Ser Leu Ala Asp Ile
785                 790                 795                 800

Met Ser Leu Trp Gly Glu Ser Glu Phe Gly Phe Trp Gly Phe Ser Ile
                805                 810                 815

Lys

<210> SEQ ID NO 15
<211> LENGTH: 36
<212> TYPE: DNA
<213> ORGANISM: Artificial
<220> FEATURE:
<223> OTHER INFORMATION: A synthetic coding sequence (FAWPEPBIN_Bac)
    encoding a FAW ABCc4 receptor binding peptide.

<400> SEQUENCE: 15
tcttctttag cagatattat gtctttatgg ggagaa                                 36

<210> SEQ ID NO 16
<211> LENGTH: 36
<212> TYPE: DNA

```
<213> ORGANISM: Artificial
<220> FEATURE:
<223> OTHER INFORMATION: A synthetic coding sequence (FAWPEPBIN_PL)
      encoding a FAW ABCc4 receptor binding peptide.

<400> SEQUENCE: 16
agctcgctgg cggacattat gtcgctgtgg ggcgaa                          36

<210> SEQ ID NO 17
<211> LENGTH: 12
<212> TYPE: PRT
<213> ORGANISM: Artificial
<220> FEATURE:
<223> OTHER INFORMATION: The FAW ABCc4 receptor binding peptide sequence
      (FAWPEPBIN) encoded by SEQ ID NO:15 and SEQ ID NO:16.

<400> SEQUENCE: 17

Ser Ser Leu Ala Asp Ile Met Ser Leu Trp Gly Glu
1               5                   10

<210> SEQ ID NO 18
<211> LENGTH: 21
<212> TYPE: DNA
<213> ORGANISM: Artificial
<220> FEATURE:
<223> OTHER INFORMATION: A DNA sequence encoding an miRNA target binding
      site, Gm.miR395_1.

<400> SEQUENCE: 18
tgaagtgttt gggggaactt c                                         21

<210> SEQ ID NO 19
<211> LENGTH: 21
<212> TYPE: DNA
<213> ORGANISM: Artificial
<220> FEATURE:
<223> OTHER INFORMATION: A DNA sequence encoding an miRNA binding target
      site, Gm.miR395_2.

<400> SEQUENCE: 19
tgaagtgttt gggggaactt g                                         21

<210> SEQ ID NO 20
<211> LENGTH: 62
<212> TYPE: DNA
<213> ORGANISM: Artificial
<220> FEATURE:
<223> OTHER INFORMATION: A DNA sequence (SUP-miR395) wherein the miRNA
      target binding sites, Gm.miR395_1 and Gm.miR395_2 are linked using
      a DNA sequence, SP-ART.8a-1.

<400> SEQUENCE: 20
gaagttcccc caaacacttc aaagtactgc gatcgcgtta acaagttccc ccaaacactt    60
ca                                                                  62

<210> SEQ ID NO 21
<211> LENGTH: 22
<212> TYPE: DNA
<213> ORGANISM: Artificial
<220> FEATURE:
<223> OTHER INFORMATION: A DNA sequence encoding an miRNA target binding
      site, Gm.miR4392_1.

<400> SEQUENCE: 21
tctgcgaaaa tgtgatttcg gc                                        22
```

```
<210> SEQ ID NO 22
<211> LENGTH: 22
<212> TYPE: DNA
<213> ORGANISM: Artificial
<220> FEATURE:
<223> OTHER INFORMATION: A DNA sequence encoding an miRNA target binding
      site, Gm.miR4392_2.

<400> SEQUENCE: 22
tgaagtgttt gggggaactt gg                                               22

<210> SEQ ID NO 23
<211> LENGTH: 64
<212> TYPE: DNA
<213> ORGANISM: Artificial
<220> FEATURE:
<223> OTHER INFORMATION: A DNA sequence (SUP-miR4392) wherein the miRNA
      target binding sites, Gm.miR4392_1 and Gm.miR4392_2 are linked
      using a DNA sequence, SP-ART.8a-1.

<400> SEQUENCE: 23
gccgaaatca cattttcgca gaaagtactg cgatcgcgtt aacccgaaat cacattttcg     60
caga                                                                  64

<210> SEQ ID NO 24
<211> LENGTH: 20
<212> TYPE: DNA
<213> ORGANISM: Artificial
<220> FEATURE:
<223> OTHER INFORMATION: The DNA sequence of the linker, SP-ART.8a-1.

<400> SEQUENCE: 24
aagtactgcg atcgcgttaa                                                  20

<210> SEQ ID NO 25
<211> LENGTH: 2490
<212> TYPE: DNA
<213> ORGANISM: Artificial
<220> FEATURE:
<223> OTHER INFORMATION: A DNA sequence (TIC7941PL_1-mi395) encoding
      TIC7941PL_1 operably linked to SUP-miR395.

<400> SEQUENCE: 25
atggctaagc agaacaacaa cctctccgtg cgcgcgctgc cgagcttcat cgacgtcttc     60
aacggcatct acgggttcgc cacgggcatc caggacatct tcaacatgat ctttgggact    120
gatacgggcg gcctgaccct ggaggaggtg ttaaagaacc aggatctcct ctacgagatt    180
tcgggcaagc tggacgggat caacggcgac ctgagcgaga tcatcgccca ggcaacctc     240 aacaccgagc tcacgaaaga actactgaag attgccaacg agcagaacaa cctgctcacg    300
gacgtgaaca caagctgaa cgccatcaac gcgatgctga cacctacct gcccaagatc     360 accaacatgc tgagcgacat catgaagcag aactacgtcc tgtcccttca gatcgagtac    420
ctgtccaagc agctccagga gatctcggac aagttggacg tgatcaacct caacgtgctc    480
atcaactcga ccctcaccga gatcactcca gcgtaccagc gcatcaagta cgtcaacgag    540
aagttcgacg acctgacgct ggccactgag aagaccctgc gcgcgaagca aggctcgtcc    600
aacgaggaca tcttcgacaa cgacacccctg gagaacctca cggagctgac cgagctggcc    660
aagagcgtga cgaagaacga cgtggactcg ttcgagttct acctccacac tttccacgac    720
gtcctgatcg ggaacaacct cttggtcgt tcggccctca gacggcggc ggagctcatc     780 acaaaggacg agatcaagac ctctgggtct gagatcggca aggtgtactc gtttctcatt    840
```

-continued

```
gtcctgacgt gcctgcaagc gaaggcttac ctaacgctca cggcgtgccg caagctgctg     900
ggcctgtctg acatcgacta caccaacatc ctgaaccagc accttaacga cgagaagaac     960
gagttccggg acaacattct tcctaccctg tcgaacaagt tcagcaaccc gaactacgcg    1020
aagaccacgg gcagcgacga cgatgcggtg gtggtcctgg aggctgacct gggctacgcg    1080
ctgatcggct tcgagatcat cagcgaccct atcccagtgc tcaaggtgta ccaggcgaag    1140
ctgaaacaga actaccaggt tgacgagcag tccctgacgg agaaggtgta ccggaacatc    1200
aataagatct tctgcccgga gaactccgac cagcggtact acatcaagga catcaccttc    1260
cctatcgggt acgtcatcac caagataatc ttcgagaaga agtaccagaa ccgactcggc    1320
tacctggtga aggcgaactt ctatgacagc tcgacgggcg acatcgacct caacaagtcc    1380
atcgaggaga gtagcgggaa tctgctggcg tggccgcccg acagcatcat ctccatctcc    1440
aaggacgagg aagacgagaa ggatgtgtac atgccactag gcgtcatctc cgaaactttc    1500
ctgacaccca tacacagctt cgggctcaag gtggacgagg agagccggat catcacgctg    1560
accggcaaga gctacctccg agagtacctg ctggagtcgg acctcaagaa caaggagacg    1620
tcgctgatcg ctcctcccaa cgtcttcatc tccaacatcg tcgagaactg aacatcgag    1680
gcggacagcc tggagccgtg ggtggcgaac aacaagaacg cttacgtgga ctcaaccggc    1740
ggcattgagg gctccaaggc cctattcacg caaggcgacg gcgagttcag ccagttcatc    1800
ggcgacaagc taaagcccaa cacgactac atgatccagt acactgtgaa gggcaagccc    1860
gcgatctacc tcaagcacaa ggacgcaacc ggctacatca tgtacgagga caccaacggc    1920
aactacgagg acttccagac gcgggccgtc aagttcacct cgggcgctga gccgtcccag    1980
gcccacttga tcttcaagtc ccagtcgggc tacgaggctt ggggcgacaa ctttatcatc    2040
ctggagagca gtcggtgga gttcgaccag aaactcgagg ctccggaggt catcaagtcg    2100
gagaactgga tactgactgg cgacgcgaag ctggaacagg acggccaggc cctgaggtcc    2160
gtgagcggga acggcagctt caagcagttc ctccagctca gtccgacag catctacttt    2220
atgaacttcc acgtcgtggg caaggcgcgc gtgactatca agaacagcca ccgcgtcctc    2280
ttcgagaagg actacagcac gcagtatcgc atagtcgatg atgaatactt caccaccgtc    2340
tccgacatcg acggcgtgtt catcgagctg acgtcgcact ccgaggagtc ctccgagttc    2400
ggcttctggg gcttcagcat caagtagtga agttccccca aacacttcaa agtactgcga    2460
tcgcgttaac aagttccccc aaacacttca                                      2490
```

<210> SEQ ID NO 26
<211> LENGTH: 2493
<212> TYPE: DNA
<213> ORGANISM: Artificial
<220> FEATURE:
<223> OTHER INFORMATION: A DNA sequence (TIC7941PL_1-mi4392) encoding TIC7941PL_1 operably linked to SUP-miR4392.

<400> SEQUENCE: 26

```
atggctaagc agaacaacaa cctctccgtg cgcgcgctgc cgagcttcat cgacgtcttc      60
aacggcatct acgggttcgc cacgggcatc caggacatct tcaacatgat ctttgggact     120
gatacgggcg gcctgaccct ggaggaggtg ttaaagaacc aggatctcct ctacgagatt     180
tcgggcaagc tggacgggat caacggcgac ctgagcgaga tcatcgccca gggcaacctc     240
aacaccgagc tcacgaaaga actactgaag attgccaacg agcagaacaa cctgctcacg     300
gacgtgaaca acaagctgaa cgccatcaac gcgatgctga cacctacct gcccaagatc     360
```

```
accaacatgc tgagcgacat catgaagcag aactacgtcc tgtcccttca gatcgagtac    420
ctgtccaagc agctccagga gatctcggac aagttggacg tgatcaacct caacgtgctc    480
atcaactcga ccctcaccga gatcactcca gcgtaccagc gcatcaagta cgtcaacgag    540
aagttcgacg acctgacgct ggccactgag aagaccctgc gcgcgaagca aggctcgtcc    600
aacgaggaca tcttcgacaa cgacaccctg gagaacctca cggagctgac cgagctggcc    660
aagagcgtga cgaagaacga cgtggactcg ttcgagttct acctccacac tttccacgac    720
gtcctgatcg ggaacaacct ctttggtcgt tcggccctca agacggcggc ggagctcatc    780
acaaaggacg agatcaagac ctctgggtct gagatcggca aggtgtactc gtttctcatt    840
gtcctgacgt gcctgcaagc gaaggcttac ctaacgctca cggcgtgccg caagctgctg    900
ggcctgtctg acatcgacta caccaacatc ctgaaccagc accttaacga cgagaagaac    960
gagttccggg acaacattct tcctaccctg tcgaacaagt tcagcaaccc gaactacgcg   1020
aagaccacgg gcagcgacga cgatgcggtg gtggtcctgg aggctgacct gggctacgcg   1080
ctgatcggct tcgagatcat cagcgaccct atcccagtgc tcaaggtgta ccaggcgaag   1140
ctgaaacaga actaccaggt tgacgagcag tccctgacgg agaaggtgta ccggaacatc   1200
aataagatct tctgcccgga gaactccgac cagcggtact acatcaagga catcaccttc   1260
cctatcgggt acgtcatcac caagataatc ttcgagaaga agtaccagaa ccgactcggc   1320
tacctggtga aggcgaactt ctatgacagc tcgacgggcg catcgaccct caacaagtcc   1380
atcgaggaga gtagcgggaa tctgctggcg tggccgcccg acagcatcat ctccatctcc   1440
aaggacgagg aagacgagaa ggatgtgtac atgccactag gcgtcatctc cgaaactttc   1500
ctgacaccca tacacagctt cgggctcaag gtggacgagg agagccggat catcacgctg   1560
accggcaaga gctacctccg agagtacctg ctggagtcgg acctcaagaa caaggagacg   1620
tcgctgatcg ctcctcccaa cgtcttcatc tccaacatcg tcgagaactg gaacatcgag   1680
gcggacagcc tggagccgtg ggtggcgaac aacaagaacg cttacgtgga ctcaaccggc   1740
ggcattgagg gctccaaggc cctattcacg caaggcgacg gcgagttcag ccagttcatc   1800
ggcgacaagc taaagcccaa cacggactac atgatccagt acactgtgaa gggcaagccc   1860
gcgatctacc tcaagcacaa ggacgcaacc ggctacatca tgtacgagga caccaacggc   1920
aactacgagg acttccagac gcgggccgtc aagttcacct cgggcgctga gccgtcccag   1980
gcccacttga tcttcaagtc ccagtcgggc tacgaggctt ggggcgacaa ctttatcatc   2040
ctggagagca gtcggtgga gttcgaccag aaactcgagg ctccggaggt catcaagtcg   2100
gagaactgga tactgactgg cgacgcgaag ctggaacagg acggccaggc cctgaggtcc   2160
gtgagcggga acggcagctt caagcagttc ctccagctca gtccgacag catctacttt   2220 atgaacttcc acgtcgtggg caaggcgcgc gtgactatca agaacagcca ccgcgtcctc   2280
ttcgagaagg actacagcac gcagtatcgc atagtcgatg atgaatactt caccaccgtc   2340
tccgacatcg acggcgtgtt catcgagctg acgtcgcact ccgaggagtc ctccgagttc   2400
ggcttctggg gcttcagcat caagtagtag ccgaaatcac attttcgcag aaagtactgc   2460
gatcgcgtta acccgaaatc acattttcgc aga                                2493
```

What is claimed is:

1. A recombinant nucleic acid molecule comprising a heterologous promoter operably linked to a polynucleotide segment encoding a pesticidal protein or pesticidal fragment thereof, wherein:
   a. said pesticidal protein comprises the amino acid sequence of SEQ ID NO:4, SEQ ID NO:2, SEQ ID NO:6, SEQ ID NO:8, SEQ ID NO:10, SEQ ID NO:12, or SEQ ID NO:14; or
   b. said pesticidal protein comprises an amino acid sequence having at least 95% amino acid sequence identity to SEQ ID NO:4, SEQ ID NO:2, SEQ ID NO:6, SEQ ID NO:8, SEQ ID NO:10, SEQ ID NO:12, or SEQ ID NO:14.

2. The recombinant nucleic acid molecule of claim 1, wherein:
   a. said recombinant nucleic acid molecule comprises a heterologous promoter sequence that functions to express the pesticidal protein in a plant; or
   b. said recombinant nucleic acid molecule is expressed in a plant cell to produce a pesticidally effective amount of the pesticidal protein or pesticidal fragment; or
   c. said recombinant nucleic acid molecule is in operable linkage with a vector, and said vector is selected from the group consisting of a plasmid, phagemid, bacmid, cosmid, and a bacterial or yeast artificial chromosome.

3. A host cell comprising the recombinant nucleic acid molecule of claim 1, wherein said host cell is selected from the group consisting of a bacterial cell and a plant cell.

4. The host cell of claim 3, wherein said bacterial host cell is from a genus of bacteria selected from the group consisting of: *Agrobacterium, Rhizobiwri, Bacillus, Brevibacillus, Escherichia, Pseudomonas, Klebsiella, Pantoea,* and *Erwinia*.

5. The host cell of claim 4, wherein said *Bacillus* species is *Bacillus cereus* or *Bacillus thuringiensis*, said *Brevibacillus* is *Brevibacillus laterosperous*, or said *Escherichia* is *Escherichia coli*.

6. A host cell comprising the recombinant nucleic acid molecule of claim 2, wherein said plant cell is selected from the group consisting of an alfalfa banana, barley, bean, broccoli, cabbage, brassica, carrot, cassava, castor, cauliflower, celery, chickpea, Chinese cabbage, citrus, coconut, coffee, corn, clover, cotton, cucurbit, cucumber, Douglas fir, eggplant, eucalyptus, flax, garlic, grape, hops, leek, lettuce, Loblolly pine, millet, melon, nut, oat, olive, onion, ornamental, palm, pasture grass, pea, peanut, pepper, pigeonpea, pine, potato, poplar, pumpkin, Radiata pine, radish, rapeseed, rice, rootstock, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

7. The recombinant nucleic acid molecule of claim 1, wherein said protein exhibits activity against a Lepidopteran insect.

8. The recombinant nucleic acid molecule of claim 7, wherein said Lepidopteran insect is selected from the group consisting of: Velvet bean caterpillar, Sugarcane borer, Lesser cornstalk borer, Corn earworm, Tobacco budworm, Soybean looper, Black armyworm, Southern armyworm, Fall armyworm, Beet armyworm, American bollworm, Oriental leaf worm, Pink bollworm, Black cutworm, Southwestern Corn Borer, Cotton leaf worm, Diamond back moth, Spotted boll worm, Tobacco cut worm, Western bean cutworm and European corn borer.

9. A plant, or part thereof, comprising the recombinant nucleic acid molecule or pesticidal protein of claim 1.

10. The plant of claim 9, wherein said plant is selected from the group consisting of: alfalfa, banana, barley, bean, broccoli, cabbage, brassica, carrot, cassava, castor, cauliflower, celery, chickpea, Chinese cabbage, citrus, coconut, coffee, corn, clover, cotton, cucurbit, cucumber, Douglas fir, eggplant, eucalyptus, flax, garlic, grape, hops, leek, lettuce, Loblolly pine, millet, melon, nut, oat, olive, onion, ornamental, palm, pasture grass, pea, peanut, pepper, pigeon pea, pine, potato, poplar, pumpkin, Radiata pine, radish, rapeseed, rice, rootstock, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

11. A seed of the plant of claim 9, wherein said seed comprises said recombinant nucleic acid molecule.

12. An insect inhibitory composition comprising the recombinant nucleic acid molecule of claim 1.

13. The insect inhibitory composition of claim 11, further comprising a nucleotide sequence encoding at least one other pesticidal agent that is different from said pesticidal protein.

14. The insect inhibitory composition of claim 13, wherein said at least one other pesticidal agent is selected from the group consisting of an insect inhibitory protein, an insect inhibitory dsRNA molecule, and an ancillary protein.

15. The insect inhibitory composition of claim 13, wherein said at least one other pesticidal agent exhibits activity against one or more pest species of the orders Lepidoptera, Coleoptera, and Hemiptera.

16. The insect inhibitory composition of claim 13, wherein said at least one other pesticidal protein is selected from the group consisting of: Cry1A, Cry1Ab, Cry1Ac, Cry1A.105, Cry1Ae, Cry1B, Cry1C, a Cry1C variant, Cry1D, Cry1E, Cry1F, a Cry1A/F chimera, Cry1G, Cry1H, Cry1I, Cry1J, Cry1K, Cry1L, Cry2A, Cry2Ab, Cry2Ae, Cry3, a Cry3A variant, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC3131, TIC2160, VIP3A, VIP3B, VIP3Ab, AXMI-001, AXMI-002, AXMI-030, AXMI-035, AXMI-036, AXMI-045, Axmi52, Axmi58, Axmi88, Axmi97, Axmi102, Axmi112, Axmi117, Axmi100, AXMI-115, AXMI-113, and AXMI-005, AXMI134, AXMI-150, Axmi171, AXMI-184, axmi196, axmi204, axmi207, axmi209, Axmi205, AXMI218, AXMI220, AXMI221z, AXMI222z, AXMI223z, AXMI224z and AXMI225z, AXMI238, AXMI270, AXMI279, AXMI335, AXMI345, AXMI-R1, an AXMI-R1 variant, IP3, an IP3 variant, DIG-3, DIG-5, DIG-10, DIG-11, DIG-657 protein, a PHI-4 variant, a PIP- 72 variant, a PIP-45 variant, a PIP-64 variant, a PIP-74 variant, a PIP-77 variant, DIG-305, a PIP-47 variant, DIG-17, DIG-90, DIG-79, and DIG-303.

17. An insect inhibitory composition comprising the recombinant nucleic acid molecule of claim 1, defined as comprising a plant cell that expresses said recombinant nucleic acid molecule of claim 1.

18. A commodity product produced from the plant, or part thereof, of claim 9, wherein said commodity product comprises a detectable amount of said recombinant nucleic acid molecule or pesticidal protein.

19. The commodity product of claim 18, selected from the group consisting of: commodity corn bagged by a grain handler, corn flakes, corn cakes, corn flour, corn meal, corn syrup, corn oil, corn silage, corn starch, corn cereal, rice flour, rice meal, rice starch, rice cereal, wheat flakes, wheat flour, wheat meal, wheat starch, wheat cereal, sorghum meal, sorghum syrup, sorghum oil, sorghum silage, sorghum cereal, pigeon pea flakes, pigeon pea flour, pigeon pea meal, pigeon pea oil, pigeon pea silage, peanut meal, peanut oil; fruit, melon, and vegetable commodity products comprising juices, concentrates, jams, jellies, marmalades; whole or processed cotton seed, cotton oil, lint, seeds and plant parts processed for feed or food, fiber, paper, biomasses, fuel products derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

20. A method of producing seed, the method comprising:
a. planting a first seed according to claim 11;
b. growing a plant or plants from said seed; and
c. harvesting seed from said plant or plants, wherein said harvested seed comprises said recombinant nucleic acid molecule.

21. A method for controlling a Lepidopteran species pest or pest infestation, said method comprising contacting the pest with a pesticidally effective amount of the pesticidal protein encoded by the recombinant nucleic acid molecule of claim 1.

22. The recombinant nucleic acid molecule of claim 1, wherein said polynucleotide segment hybridizes under stringent hybridization conditions to a polynucleotide having the nucleotide sequence of SEQ ID NO:3, SEQ ID NO:1, SEQ ID NO:5; SEQ ID NO:7, SEQ ID NO:9, SEQ ID NO:11, or SEQ ID NO:13.

23. The recombinant nucleic acid molecule of claim 1, wherein said pesticidal protein comprises the amino acid sequence of SEQ ID NO:4, SEQ ID NO:2, SEQ ID NO:6, SEQ ID NO:8, SEQ ID NO:10, SEQ ID NO:12, or SEQ ID NO:14.

*